US008822661B2

(12) United States Patent
Zhao et al.

(10) Patent No.: US 8,822,661 B2
(45) Date of Patent: Sep. 2, 2014

(54) XYLOSE REDUCTASE MUTANTS AND USES THEREOF

(75) Inventors: Huimin Zhao, Champaign, IL (US); Nikhil Unni Nair, Urbana, IL (US)

(73) Assignees: The Board of Trustees of the University of Illinois, Champaign, IL (US); Biotechnology Research and Development Corporation, Peoria, IL (US)

( * ) Notice: Subject to any disclaimer, the term of this patent is extended or adjusted under 35 U.S.C. 154(b) by 807 days.

(21) Appl. No.: 12/667,269

(22) PCT Filed: Jul. 10, 2008

(86) PCT No.: PCT/US2008/069657
§ 371 (c)(1),
(2), (4) Date: Feb. 16, 2010

(87) PCT Pub. No.: WO2009/009668
PCT Pub. Date: Jan. 15, 2009

(65) Prior Publication Data
US 2010/0291645 A1      Nov. 18, 2010

Related U.S. Application Data

(60) Provisional application No. 60/949,387, filed on Jul. 12, 2007.

(51) Int. Cl.
*C12N 15/53* (2006.01)
*C12N 9/04* (2006.01)

(52) U.S. Cl.
CPC .................................. *C12N 9/0006* (2013.01)
USPC ........................................ 536/23.2; 435/190

(58) Field of Classification Search
CPC .................................................... C12N 9/0006
See application file for complete search history.

(56) References Cited

U.S. PATENT DOCUMENTS

| | | | |
|---|---|---|---|
| 5,096,820 A * | 3/1992 | Leleu et al. | 435/158 |
| 6,582,944 B1 | 6/2003 | Hallborn et al. | |
| 7,381,553 B2 * | 6/2008 | Zhao et al. | 435/189 |
| 2006/0035353 A1 | 2/2006 | Zhao et al. | |
| 2007/0128706 A1 | 6/2007 | Gorwa-Grauslund et al. | |

OTHER PUBLICATIONS

B. Hacker et al. "Xylose Utilisation: Cloning and Characterisation of the Xylose Reductase from *Candida tenuis*", Biol. Chem. 380:1395-1403 (Dec. 1999).*

Woodyer et al., "Heterologous Expression, Purification, and Characgerization of a Highly Active Xylose Reductase from *Neurospora crassa*," *Appl. and Env. Microbio.*, 71(3): 1642-1647 (2005).
International Search Report issued in application No. PCT/US08/69657 (2008).
Database UniProt (2004): "Hypothetical protein (Xylose reductase)," Accession No. Q7SD67.
Database EMBL-EBI (2000): "*Aspergillus niger* D-xylose reductase (xyrA) gene, complete cds," Accession No. AF219625.
Haldimann et al., Conditional-replication, integration, excision, and retrieval plasmid-host systems for gene structure-function studies of bacteria, *J Bacteriol.*, 183(21):6384-93 (2001).
Hasper et al., "The *Aspergillus niger* transcriptional activator XInR, which is involved in the degradation of the polysaccharides xylan and cellulose, also regulates D-xylose reductase gene expression," *Molecular Microbiology*, 36 (1): 193-200 (2000).
Ikemi et al., "Sorbitol Production in Charged Membrane Bioreactor with Coenzyme Regeneration System: I. Selective Retainment of NADP(H) in a Continuous Reaction," *Biotechnology and Bioengineering*, 36: 149-154 (1990).
Jin et al., "Molecular cloning of XYL3 (D-xylulokinase) from *Pichia stipitis* and characterization of its physiological function," *Appl. Environ. Microbiol.*, 68 (3): 1232-1239 (2002).
Kavanagh et al., "Structure of xylose reductase bound to NAD+ and the basis for single and dual co-substrate specificity in family 2 aldo-keto reductases," *Biochem J.*, 373 (Pt 2): 319-326 (2003).
Klimacek et al., "Exploring the active site of yeast xylose reductase by site-directed mutagenesis of sequence motifs characteristic of two dehydrogenase/reductase family types" *FEBS Letters*, 500(3): 149-152 (2001).
Klimacek et al., "Role of Phe-114 in substrate specificity of *Candida tenuis* xylose reductase (AKR2B5)," *Biocatalysis And Biotransformation*, 25 (2-4): 194-201 (2007).
Kozma et al., "The crystal structure of rat liver AKR7A1. A dimeric member of the aldo-keto reductase superfamily," *J. Biol. Chem.*, 277 (18): 16285-16293 (2002).
Nair et al., "Evolution in reverse: engineering a D-xylose-specific xylose reductase," *Chembiochem*, : A European Journal of Chemical Biology 9(8): 1213-1215 (2008).
Neuhauser et al., "NAD(P)H-dependent aldose reductase from the xylose-assimilating yeast *Candida tenius*. Isolation, characterization and biochemical properties of the enzyme," *Biochem. J.*, 326 (Pt 3): 683-692 (1997).
Nidetzky et al., "Continuous Enzymatic Production of Xylitol with Simultaneous Coenzyme Regneration in a Charged Membrane Reactor," *Biotechnology and Bioengineering*, 52: 387-396 (1996).
Rawat et al., "Conformation and microenvironment of the active site of xylose redutase inferred by fluorescent chemoaffinity labeling," *Eur. J. Biochem.*, 243: 344-349 (1997).
Rawat et al., "D-xylose catabolizing enzymes in *Neurospora crassa* and their relationship to D-xylose fermentation," *Biotechnology Letters*, 15 (11): 1173-1178 (1993).
Rawat et al., "Purification, kinetic characterization and involvement of tryptophan residue at the NADPH binding site of xylose reductase from *Neurospora crassa*," *Biochimica et Biophysica Acta*, 1293: 222-230 (1996).

(Continued)

*Primary Examiner* — Rebecca Prouty
(74) *Attorney, Agent, or Firm* — McDonnell Boehnen Hulbert & Berghoff LLP

(57) ABSTRACT

Engineered mutant xylose reductases demonstrate higher preference to xylose than arabinose. Amino acid mutations were engineered in to native xylose reductase from *Neurospora crassa*. Mutant xylose reductases are useful in the production of xylitol and ethanol.

1 Claim, 6 Drawing Sheets

(56) References Cited

OTHER PUBLICATIONS

Rawat et al., "Site and Significance of Cysteine Residues in Xylose Reductase from *Neurospora crassa* as Deduced by Fluorescence Studies," *Biochemical and Biophysical Research Communications*, 239 (3): 789-793 (1997).

Watanabe et al, "The positive effect of the decreased NADPH-preferring activity of xylose reductase from *Pichia stipitis* on ethanol production using xylose-fermenting recombinant *Saccharomyces cerevisiae*," *Bioscience Biotechnology Biochemistry*, 71(5): 1365-1369 (2007).

Zhao et al., "The Production and Properties of a New Xylose Reductase from Fungus: *Neurospora Crassa*," *Applied Biochemistry and Biotechnology*, 70-72: 405-414 (1998).

Search Report issued in application No. EP08796144 (2010).

* cited by examiner

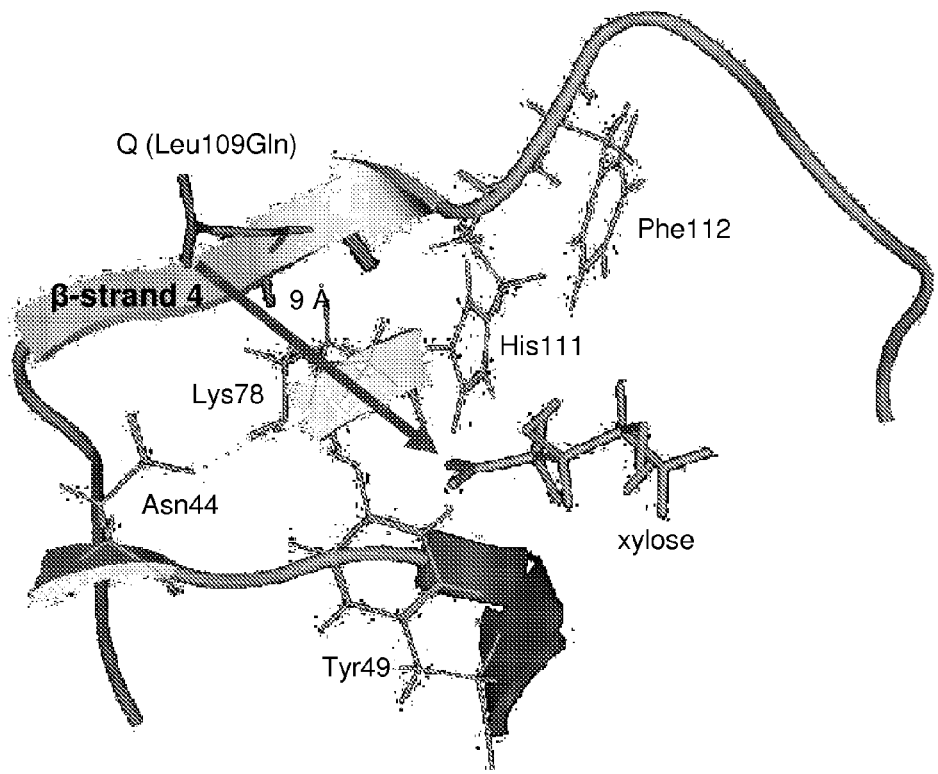

FIG. 8

```
C_tenuis_XR          DLKVDYVDLFLIHFPIAFKFVPIEEKYPPGFYCGDGNNFVYED-VPILET
P_stipitis_XR        DLQVDYVDLFLIHFPVIFKFVPLEEKYPPGFYCGKGDNFDYED-VPILET
C_tropicalis_XR      DLNLDYVDLFLIHFPIAFKFVPIEEKYPPGFYCGDGDNFHYED-VPLLDT
C_albicans_XR        DLNLEYLDLFLIHFPIAFKFVPLEEKYPPGFYCGDGDKFHYEN-VPLLDT
P_guilliermondii_XR  DLKVDYLDLFLIHFPIAFKFVPFEEKYPPGFYCGDGDKFTYED-VPIIDT
A_niger_XR           DWGIDYFDLYIVHFPISLKYVDPAVRYPPGWKSEKD-ELEFGN-ATIQET
A_terreus_XR         DWGVDYFDLYIVHFPVALKYVDPAVRYPPGWSAKGDGSIEFSN-ASIQET
H_jecorina_XR        DWQIDYFDLFLVHFPAALEYVDPSVRYPPGWFYDGKSEVRWSKITTLQQT
NcXR_WT              DWGLEYFDLYLIHFPVALEYVDPSVRYPPGWHFDGKSEIRPSK-ATIQET
                     *  ::*.**::: ***  ::: *   :****:   ..  .  ..: :*
NcXR_VMQCI           DWGVEYFDMVQCHFFIALEYVDPSVRYPPGWHFDGKSEIRPSK-ATIQET
                        |                |
                        102              118
```

FIG. 9

XYLOSE REDUCTASE MUTANTS AND USES THEREOF

CROSS-REFERENCE TO RELATED PATENT APPLICATIONS

This application is a U.S. Nationalization under 35 U.S.C. §371 of international patent application no. PCT/US2008/069657, filed Jul. 10, 2008, which claims priority to U.S. application no. 60/949,387, filed Jul. 12, 2007, the contents of which applications are herein incorporated by reference in their entireties.

BACKGROUND

Xylose reductase mutants with improved specificity towards xylose and their uses are described.

Xylitol (1) is a pentitol and is used not only as a sweetener but also as a platform chemical for the production of industrially important chemicals. Studies have shown that among sugar substitutes, xylitol is one of the most promising candidates for application in a wide range of products due to several favorable properties. These include anti-cariogenicity, suitability for use by diabetic patients, and good gastrointestinal tolerance, in addition to possibly preventing osteoporosis and ear infections. In spite of its advantages, the use of xylitol is currently limited and falls well short of another, cheaper sugar alternative, sorbitol in the billion dollar polyol market. Other than its use as a sweetener, xylitol is also an industrially important chemical, and the US Department of Energy (DOE) has named it among one of their top 12 platform chemicals from agricultural sources.

Xylose reductase (XR) is an enzyme found commonly in yeast and fungal organisms often with several isozymes in the same species. This enzyme catalyzes the first step in the metabolism of D-xylose and other pentose sugars by reducing the linear aldehyde form of the sugar to xylitol (or a corresponding sugar alcohol). Xylitol can then be oxidized to xylulose by NAD-dependent xylitol dehydrogenase and phosphorylated by D-xylulokinase. The resulting sugar phosphate can enter the pentose phosphate pathway. The reversible reduction of xylitol by XR occurs concomitantly with NAD(P)H oxidation. In general, XR is specific for NADPH, but in some cases it utilizes both NADPH and NADH and in at least one case prefers NADH over NADPH. The different forms of XR in the same species usually have different cofactor preferences and they are likely needed to maintain the redox balance between nicotinamide cofactors under a variety of growth conditions. In order to maintain this balance under anaerobic conditions, XR is likely to be NADH-dependent because the enzyme in the following step (xylitol dehydrogenase) is NAD specific. However, under aerobic conditions either cofactor can be used since cofactors can be regenerated. Some yeast species have solved this problem by utilizing one form of XR with dual cofactor specificity.

Commercially available xylitol is obtained by processing its oxidized form, the pentose D-xylose. Second only to glucose, xylose is the most common sugar in nature, and is the primary component of plant hemicellulose. Unlike cellulose, which is a homogenous glucose polymer, hemicelluloses are complex polymers of several sugars (D-xylose, L-arabinose, D-glucose, D-mannose, and D-galactose, etc.) and sugar acids. Xylose is purified from pretreated hemicellulose and then chemically reduced to xylitol at high pressure (40 atm), high temperature (135° C.) with elemental hydrogen over a carcinogenic Raney-Nickel catalyst. Recent studies have tried to formulate several safer and environmentally friendlier techniques based on biotechnology to produce xylitol using a xylose reductase enzyme (XR). However, the techniques previously described require the use of purified xylose, due to the promiscuous nature of XRs toward sugars found in hemicellulose. Separating xylose from arabinose is particularly difficult, being epimers and having the same molecular weight. In addition all known catalysts, whether enzymatic XRs or synthetic Raney-Nickel, can reduce both sugars efficiently.

One alternative to purifying xylose from impurities is to engineer an XR to preferentially utilize xylose, or more simply, to engineer an XR to accept arabinose poorly compared to xylose. Such an enzyme would negate the need for extensive purification of xylose prior to reduction, increasing yield and simultaneously decreasing production costs.

SUMMARY

Xylose reductase (XR) mutants that preferentially utilize D-xylose are described. For example, mutants designated as "S" and "VMQCI" have approximately 14-fold and 16-fold preference, respectively, for D-xylose compared to L-arabinose.

Mutant XRs disclosed herein are used in either a heterologous host such as *E. coli* or *S. cerevisiae*, or as a purified enzyme in a continuous flow membrane reactor, to selectively reduce xylose into xylitol from a mixture of several sugars. These sugars include for example xylose, arabinose, ribulose, glucose, mannose, galactose, or any other components of plant hemicellulose in any combination. The specific reduction of xylose from a mixture of sugars minimizes the need of extensive purification and minimizes the cost of expensive purification of xylose from other sugars, particularly pentoses, which have very similar physical properties.

A combined structure-function based semi-rational design involving sequential rounds of saturation mutagenesis of targeted residues and screening for decreased arabinose to xylose relative enzymatic efficiency, and several rounds of random point mutagenesis and selection for desired substrate specificity was implemented and described herein.

Purified mutant xylose reductases that are more specific to xylose compared to a wild-type xylose reductase from *Neuorospora crassa*, wherein the mutant xylose reductase includes a mutation in an amino acid sequence LEYFDLYLIHFPVA-LEY (amino acids 102-118 of SEQ ID NO: 1) selected from L102V, L107M, L109Q, I110C, F112S, and V114I.

A purified mutant xylose reductase is more specific to xylose compared to a wild-type xylose reductase from *Neuorospora crassa*. In an aspect, the mutant xylose reductase includes an amino acid sequence of SEQ ID NO: 1, wherein the amino acid at position 112 is Ser (S) instead of Phe (F).

A mutant xylose reductase includes an amino acid sequence of SEQ ID NO: 1, wherein the amino acid at position 109 is Gln (Q) instead of Leu (L). In an aspect, the mutant xylose reductase, at position 110 of SEQ ID NO: 1, has a Cys (C) instead of Ile (I).

A mutant xylose reductase, with reference to SEQ ID NO: 1, at position 110 has Cys (C) instead of Ile (I); at position 107 has Met (M) instead of Leu (L); at position 114 has Ile (I) instead of Val (V); and at position 102 has Val (V) instead of Leu (L).

A purified xylose-specific mutant xylose reductase includes an amino acid sequence of SEQ ID NO: 1, wherein an amino acid mutation is selected from: amino acid at position 112 is Ser (S) instead of Phe (F); amino acid at position 109 is Gln (O) instead of Leu (L); amino acid at position 110 is Cys (C) instead of Be (I); at position 107 is Met (M) instead of Leu (L); at position 114 is Ile (I) instead of Val (V); and at position 102 is Val (V) instead of Leu (L).

A purified xylose reductase is 95% or 97% or 99% similar to SEQ ID NO: 1.

A mutant xylose reductase includes naturally occurring variations in *N. crassa* xylose reductase. A xylose reductase may be recombinant and may contain a fusion protein.

A xylose reductase is about 5-fold or 10-fold, 14-fold, 16-fold, or 20-fold more specific to xylose than arabinose.

A purified mutant xylose reductase is about 90% or 95% pure. In an aspect, the xylose reductase is purified from a heterologous host and heterologous host is selected from bacteria, yeast, and plants.

The xylose reductase mutants described herein are used to produce a sugar alcohol, sorbitol, xylitol, ethanol and may also involve a phosphite dehydrogenase-based NADP regeneration system. The production process may involve a fermentation process.

A purified mutant xylose reductase metabolically enhances an organism used for fermentation of a plant biomass to produce ethanol.

A method of producing ethanol includes:
(a) obtaining a mutant xylose reductase; and
(b) providing conditions to produce ethanol from a xylose containing medium.

A method of producing xylitol includes:
(a) obtaining a mutant xylose reductase; and
(b) providing conditions to produce xylitol from a xylose containing medium.

The method of producing xylitol and ethanol may include the use of a phosphite dehydrogenase (PTDH) for co-factor regeneration.

Suitable heterologous hosts include *Escherichia coli, Saccharomyces cerevisiae*, and a plant cell.

BRIEF DESCRIPTION OF THE DRAWINGS

FIG. 8 shows mapping Q mutation on NcXR homology model. Leu109Gln is indicated. Conserved active amino acid residues are shown. His111 and Phe112 are also indicated in proximity of β-strand 4.

FIG. 9 shows Multiple-Sequence Alignment (MSA) of several known fungal and yeast XRs (SEQ ID NOS105-112, Residues 99-147 of SEQ ID NO: 1 and SEQ ID NO: 113, respectively, in order of appearance).* fully conserved residues, conservation of strong groups, conservation of weak groups, all others are not conserved. Mutations in VMCQI (underlined) are distributed among three of the four conservation groups. Residues targeted for mutation on and flanking β-strand 4 are between 102 and 118.

DETAILED DESCRIPTION

Figure 1:
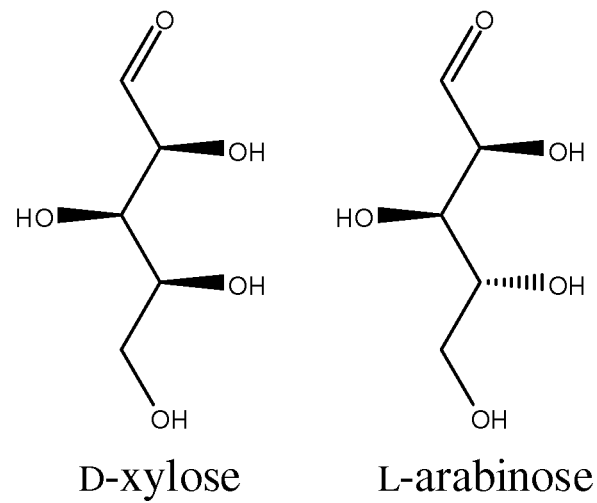
FIG. 1 shows comparison of XR sugar substrate epimers D-xylose and L-arabinose.

Purified mutant xylose reductases that are more specific to xylose compared to wild-type xylose reductase from *Neuorospora crassa* are disclosed, wherein the mutant xylose reductases include one or more mutations in an amino acid sequence LEYFDLYLIHFPVALEY (amino acids 102-118 of SEQ ID NO: 1) selected from the group of L102V, L107M, L109Q, I110C, F112S, and V114I. For example, purified mutant xylose reductases consist essentially of amino acids 102-118 of SEQ ID NO: 1 along with amino acid sequence required for reducing xylose to xylitol and any other sequence that does not materially affect the main function of the xylose reductase fragment.

Mutant xylose reductases include an amino acid sequence of SEQ ID NO: 1, wherein the amino acid at position 102 is Val (V) instead of Leu (L); at position 107 is Met (M) instead of Leu (L); at position 110 is Cys (C) instead of Ile (I); and at position 114 is Ile (I) instead of Val (V).

Purified mutant xylose reductases have a $K_m$ of at least 100 mM for xylose or at least 200 mM or at least 250 mM. Mutant xylose reductases are selective for xylose at least 5-fold or 10-fold or 12-fold or 15-fold or 16-fold as compared to arabinose. Fold-comparisons are made with respect to L-arabinose (see Table 5), because wild-type xylose reductase acts on arabinose as well.

Purified xylose-specific mutant xylose reductases include an amino acid sequence of SEQ ID NO: 1, wherein an amino acid mutation is selected from: amino acid at position 112 is Ser (S) instead of Phe (F); amino acid at position 109 is Gln (O) instead of Leu (L); amino acid at position 110 is Cys (C) instead of Ile (I); at position 107 is Met (M) instead of Leu (L); at position 114 is Ile (I) instead of Val (V); and at position 102 is Val (V) instead of Leu (L).

In certain embodiments, purified mutant xylose reductases are about 95% similar to SEQ ID NO: 1 and may include naturally occurring variations in *N. crassa* xylose reductase. In certain embodiments, xylose reductases disclosed herein are recombinant and/or expressed or purified from a heterologous host. Suitable heterologous hosts include for example, bacteria, yeast, and plants or plant cells. Cultures of bacteria, yeast, and plant cells in a batch reactor or a continuous flow reactor are also suitable for large-scale xylose reductase production.

In certain embodiments, purified xylose reductase mutants disclosed herein are about 90% pure, or 95% pure or about 98% pure and generally more than about 90% pure.

Mutant xylose reductases disclosed herein are capable being expressed in a variety of heterologous hosts such as bacteria, fungi, and plants. Such hosts include for example, *Escherichia coli, Saccharomyces cerevisiae*, and a plant cell. In certain embodiments, the heterologous hosts are engineered for increased xylose uptake. Because the xylose reductase mutants are more specific to xylose than other related sugars, the substrate or the source material need not be extensively or substantially purified for xylose and can include mixtures of sugars as found in plant biomass material.

A method of producing xylitol includes:
(a) obtaining a mutant xylose reductase disclosed herein;
(b) providing a substrate that includes xylose; and
(b) providing conditions to produce xylitol from the xylose containing substrate.

In an aspect, xylose reductase is expressed in a heterologous host in a fermentation process. Xylitol production may also include the use of a phosphite dehydrogenase (PTDH)-based NADP co-factor regeneration. Examples of NADP co-factor regeneration are found e.g., in US-2004-0091985-A1 (U.S. Ser. No. 10/371,701) to Metcalf et al., the contents of which are incorporated herein by reference in its entirety.

Methods for producing ethanol using xylose reductase and one or more other constituents such as xylitol dehydrogenase are also disclosed.

A method of producing a sugar alcohol includes:
(a) obtaining a mutant xylose reductase disclosed herein;
(b) providing a substrate that includes xylose; and
(c) providing conditions to produce a sugar alcohol from the xylose containing substrate.

A suitable sugar alcohol is sorbitol and the production of sugar alcohol may be by fermentation.

Providing conditions refer to providing suitable substrate, cofactor, catalysts, temperature, nutrients for organisms if used, pH, and other conditions necessary for enzyme catalysis or culturing heterologous hosts having the xylose reductase mutants described herein.

Isolated nucleic acid sequences encode the mutant xylose reductases disclosed herein. SEQ ID NO: 2 disclosed herein is used as a template to generate the mutants disclosed herein. Codons for the various amino acids are well known and are used in generating mutant nucleic acid sequences. The xylose reductases disclosed herein are capable of being expressed in a heterologous host e.g., E. coli, yeast, and a plant cell. Nucleic acid sequences for the mutants may optionally include a nucleic acid sequence encoding a purification tag sequence. Suitable tags for purification include for example His-tag, GST, MBP, FLAG, HPC, CBP, CYD (covalent yet dissociable NorpD peptide), and Strep II.

Mutant XRs are engineered to prefer d-xylose over L-arabinose for circumventing purification issues during biosynthesis of xylitol. β-strand 4 in the $(\beta/\alpha)_8$ structure of XR plays an important role in discriminating sugar substrates. D-xylose and L-arabinose transporters can be targeted to modulate intracellular concentrations of sugars to further enhance the effects of mutant VMQCI.

To engineer XR mutants, identification of an appropriate template of XR is required. The XR from the filamentous fungus Neurospora crassa (NcXR) has been identified as one the most active XR to date (TABLE 1). In addition, the protein has several other favorable properties such as high level of heterologous soluble expression in E. coli and innate higher than twofold preference of xylose when compared to arabinose (TABLE 2). Enzymes involved in sugar metabolism have evolved to accept a broad range of substrates to provide organisms a competitive advantage in various environments where nutrition is limited. Where substrates are epimeric (FIG. 1), it is a challenge to engineer mutations to change enzyme specificity.

Two different approaches were utilized to create a more xylose specific XR compared to the wild-type. The first involved saturation mutagenesis of targeted residues identified as important for substrate specificity based on structural analysis of the homology model. The second involved random mutagenesis throughout the xylose reductase gene.

In one approach, residues that directly interact with the substrate were mutated. Eleven independent libraries were created each with a single position randomized using NNS primers to maximize all sense codon representations. Since the sites were mutated individually, the overall diversity was limited to 20 per library. Such a library was therefore small enough to be manually screened using a 96-well plate assay, providing a quantitative assessment of the mutants' selectivity. To ensure a reasonable assurance of complete coverage of all mutants, about 150 mutants were screened per library. One of the mutants was designated as "Mutant S" that had a mutation Phe112Ser, had a significant (~5.5-fold) increase in selectivity as determined by a ratio of catalytic efficiency between xylose and arabinose. This mutation also affected the activity toward xylose, dropping the catalytic efficiency almost 14-fold. Nevertheless, since selectivity is of greater importance, the loss in activity was acceptable. A second round of mutagenesis was performed on the remaining ten residues over the S template.

In another approach, random mutagenesis was used to identify mutations outside the substrate interacting region that may contribute to improved selectivity toward xylose. Random mutations were introduced on the S template by error-prone polymerase chain reaction (epPCR) to create a library of greater than $10^5$ individual mutants.

To achieve a desired diversity in the mutant library on the wild-type NcXR template, it was necessary to optimize the level of mutagenesis, or more exactly, the average number of mutations per gene. EpPCR is a suitable standard method for introducing random point mutations, the frequency of which can be controlled. By adjusting the concentration of $Mn^{2+}$ ion in the reaction mix, and providing unequal concentrations of the four dNTPs, various levels of mutations can be introduced into a newly synthesized gene from a template (see for example, Beckman et al., On the Fidelity of DNA-Replication—Manganese Mutagenesis Invitro. *Biochemistry*, 24(21), 5810-5817, 1985). It is generally desirable to have a library with approximately 50% active mutants, which generally corresponds to 1-2 amino acid substitutions per mutant gene. Three libraries were created with 0.1 mM, 0.2 mM, and 0.3 mM $Mn^{2+}$ and 93 colonies of transformants from each were tested for activity. Results indicated that using 0.2 mM $Mn^{2+}$ produces ~50% active mutants.

With a protein size of 323 amino acids, the maximum diversity is predicted at about 6,500 assuming single amino acid substitution per clone. However due to the nature of epPCR, the likelihood of 2-3 consecutive base changes for complete randomization of a single residue, is less. In addition, the degeneracy of the codons further limits the maximum number of attainable amino acid substitutions at any position, averaging at only 6 possible substitutions per position. Such a bias makes the maximum diversity about 2,000 for single amino acid substitution or about 11,000 for two amino acid substitutions. Therefore a library of $>10^5$ would easily be able to cover all possible mutations available to epPCR. This logic and conditions were applied to the epPCR performed on the mutant S background described above as well; although the test for number of active clones as a function of $Mn^{2+}$ concentration was assumed the same as wild-type.

A library of $>10^5$ was created on the wild-type background using 0.2 mM $Mn^{2+}$ for epPCR and was selected on media. Screening transformants yielded a new xylose reductase mutant, designated as "Mutant Q", which showed increased xylose specificity. Characterization of Q (corresponding to mutation Leu109Gln) revealed that it had indeed improved xylose to arabinose preference. Since epPCR can probe only a limited sequence space at each position, a library randomizing Leu109 was screened, however, a better substitution was not found.

With the identification of two positions (Phe112 and Leu109) each providing improved substrate specificity; to see whether the two mutants could be combined additively or synergistically, double mutations were created. Screening double mutant libraries randomized at positions Leu109 or Phe112 individually, on either mutant background, and simultaneously on wild-type background yielded only epistatic or antagonistic mutants. This result confirmed that the mutations were context dependent, and explained why epPCR on the S background did not identify beneficial mutations at residue Leu109.

Mapping the location of Q mutation on the NcXR homology model revealed that it was approximately 9 Å from the substrate xylose (FIG. 8). Further, its location on the same β-strand as Phe112 suggested that it may play an important role in substrate binding. Data indicated that β-strand 4 in the $(\alpha/\beta)_8$ structure of XRs may be crucial to substrate binding and specificity.

Mutagenesis thereafter included residues on and flanking this β-strand 4. Initially, only one residue (Ile110) was mutated along with all substrate interacting sites. With the identification of mutant QC (bearing the additional mutation Ile110Cys) with improved specificity, it was decided to include residues on β-strand 4 (Leu102-Tyr118). Third, fourth, and fifth rounds of saturation mutagenesis identified MQC (Leu107Met), MCQI (Val114Ile), and VMQCI (Leu102Val), respectively. This mutant (designated as VMQCI), with five substitutions, displayed 16-fold preference for xylose over arabinose, although it also displayed approximately 7-fold decrease in catalytic efficiency toward xylose. When compared to mutant S, VMQCI retains higher overall activity and also increased substrate specificity. Analysis of mutations via multiple sequence alignment with other known XRs revealed that they were distributed among fully conserved (Leu107), strongly conserved (Leu102, Leu109, Ile110) and non-conserved groups (Val114) (FIG. 9). The mode of action of each substitution in increasing the overall specificity toward xylose is analyzed with a crystal structure, and may directly or indirectly mold the shape of the catalytic pocket to offer greater steric hindrance to the C4 hydroxyl group of L-arabinose.

A suitable region for mutating wild-type *N. crassa* xylose reductase is an amino acid sequence LEYFDLYLIHFPVALEY (amino acids 102-118 of SEQ ID NO: 1). The amino acid at a position such as for example, 102 or 103 or 104 or 105 or 106 or 107 or 108 or 109 or 110 or 111 or 112 or 113 or 114 or 115 or 116 or 117 or 118 or combination thereof is mutated to obtain a xylose reductase mutant. Mutations include substitutions, deletions or additions. One such example is a mutant designated "VMQCI" consisting essentially of an amino acid sequence V̱EYFDM̱YQCHFP̱IALEY (amino acids 102-118 of SEQ ID NO: 1), wherein the mutated amino acids compared to the wild-type sequence are underlined.

The term "consisting essentially of" refers to a conserved portion of xylose reductase that includes one or more amino acid mutations disclosed herein that improve the selectivity of xylose reductases to xylose. For example, FIG. 9 shows a multiple sequence alignment showing conserved residues from a variety of xylose reductases and TABLE 4 lists some of the functions of the various residues, thus providing a structure-function relationship. Thus, the term consisting essentially of refers to that portion of the xylose reductase that is able to catalytically reduce xylose and include one or more mutations to improve xylose specificity.

Microbes are engineered that produce bulk amounts of xylitol, wherein the engineered microbes express at least one reductase and/or dehydrogenase during the synthesis of xylitol. In certain embodiments, microbes are engineered to express xylose reductases (also referred to herein as XRs) and xylitol dehydrogenase (also referred to herein XDH) enzymes to produce xylitol from xylose (or xylulose) in vivo. For example, *E. coli* are constructed to express XDH and/or XR to produce xylitol from a substrate that includes xylose (or xylulose). Certain embodiments also provide engineered microbes capable of deriving reducing equivalents from carbon substrates (such as glucose) for the subsequent reduction of xylose or xylulose to xylitol.

As used herein, the terms gene and polynucleotide sequence are used interchangeably. Nucleotide sequences that encode for or correspond to a particular sequence of nucleic acids (such as ribonucleic acids) or amino acids that include all or part of one or more products (such as polypeptides, proteins, or enzymes), and may or may not include regulatory sequences, such as promoter sequences, which determine, for example, the conditions under which the gene is expressed. *E. coli* cannot naturally synthesize (or metabolize) xylitol. Xylitol production is possible by either expression of xylose reductase for direct reduction of xylose, or expression of the reversible xylitol dehydrogenase, whereby xylulose is reduced to xylitol (see FIG. 6). Microbes are engineered to constitutively uptake xylose in the production of xylitol.

In certain embodiments, a method is provided for using transformed *E. coli* to produce xylitol from sources comprising xylose alone or in combination with other carbon substrates (such as glucose). Engineered *E. coli* constitutively uptake xylose due to the replacement of the native crp gene with a mutant gene (whose mutations correspond to three amino acid substitutions) encoding a cAMP-independent CRP variant. [see for example, methods disclosed by Eppler T and W Boos, Molecular Microbiology, 33:1221-1231 (1999)]. Such engineered *E. coli*, which express CRP* are able to take up xylose in the presence of glucose during xylitol production. Such *E. coli* express a reductase and/or dehydrogenase necessary for the synthesis of xylitol. Thus, methods for the bioproduction of xylitol from xylose-based sources using engineered microbial strains are disclosed. The *E. coli* strains disclosed herein are particularly useful for the conversion of sugar mixtures comprising xylose into value-added products (such as xylitol). Engineered *E. coli* strains also allow for transcription of xylose transporter genes (and/or genes that code for transporters capable of allowing xylose uptake).

In some embodiments, the *E. coli* strain engineered to express mutant xylose reductase from *N. crassa*, is further engineered to additionally contain a dehydrogenase necessary for the synthesis of ethanol.

In some embodiments purified xylose reductases are directly used in a reactor, e.g., a continuous membrane flow reactor to synthesize xylitol from xylose containing substrate.

A variety of microorganisms that may be used as the source of the gene encoding xylulokines, XR, and/or XDH include for example, *Gluconobacter cerinus, Gluconobacter oxydans, Acetobacter aceti, Acetobacter liquefaciens, Acetobacter pasteurianus, Frateuria aurantia, Bacillus subtilis, Bacillus megaterium Proteus rettgeri, Serratia marcescens, Corynebacterium callunae, Brevibacterium ammoniagenes, Flavobacterium aurantinum, Flavobaterium rhenanum Pseudomonas badiofaciens, Pseudomonas chlororaphis,*

Pseudomonas iners, Rhodococcus rhodochrous, Achromobacter viscosus, Agrobacterium tumefaciens, Agrobacterium radiobacter, Arthrobacter paraffineus, Arthrobadter hydrocarboglutamicas, Azotobacter indicus, Brevibacterium ketoglutamicum, C. boidinii, Corynebacterium faciens, Erwinia amylovora, Flavobacterium peregrinum, Flavobacterium fucatum, Micrococcus sp. CCM825, Nocardia opaca, Planococcus eucinatus, Pseudomonas synxantha, Rhodococcus erythropolis, Morganella morganii, Actinomadura madurae, Actinomyces violaceochromogenes, Streptomyces coelicolor, Streptomyces flavelus, Streptomyces griseoulus, Streptomyces lividans, Streptomyces olivaceus, Streptomyces tanashiensis, Streptomyces virginiae, Streptomyces antibioticus, Streptomyces cacaoi, Streptomyces lavendulae, Pichia stipitis and so forth.

Among the aforementioned microorganisms, the nucleotide sequences of the genes encoding xylitol dehydrogenase (XDH) derived from, for example, Pichia stipitis or Morganella morganii (DDBJ/GenBank/EMBL Accession No. L34345) have been reported, and therefore a gene encoding xylitol dehydrogenase can be obtained by synthesizing primers based on the nucleotide sequences of these genes encoding xylitol dehydrogenase, and performing polymerase chain reaction (PCR) using chromosomal DNA of microorganisms such as Morganella morganii ATCC 25829 as a template.

The following examples are for illustrative purposes only and are not intended to limit the scope of the disclosure.

EXAMPLE 1

Heterologous, Tunable Expression of NcXR in E. coli

Figure 2:
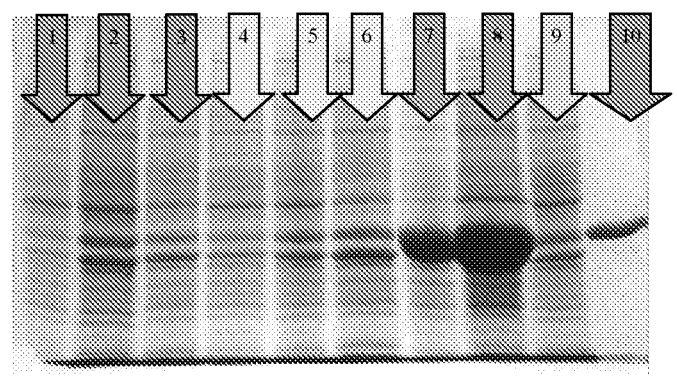
FIG. 2 shows SDS-PAGE analysis to check NcXR expression using pTrc99A (lanes 1, 2, 3), pKK223-3 (lanes 4, 5, 6), both in WM1788, and pET15b in BL21 (DE3) (lane 7, 8). Negative control (lane 9), and purified NcXR (lane 10).
Figure 3:
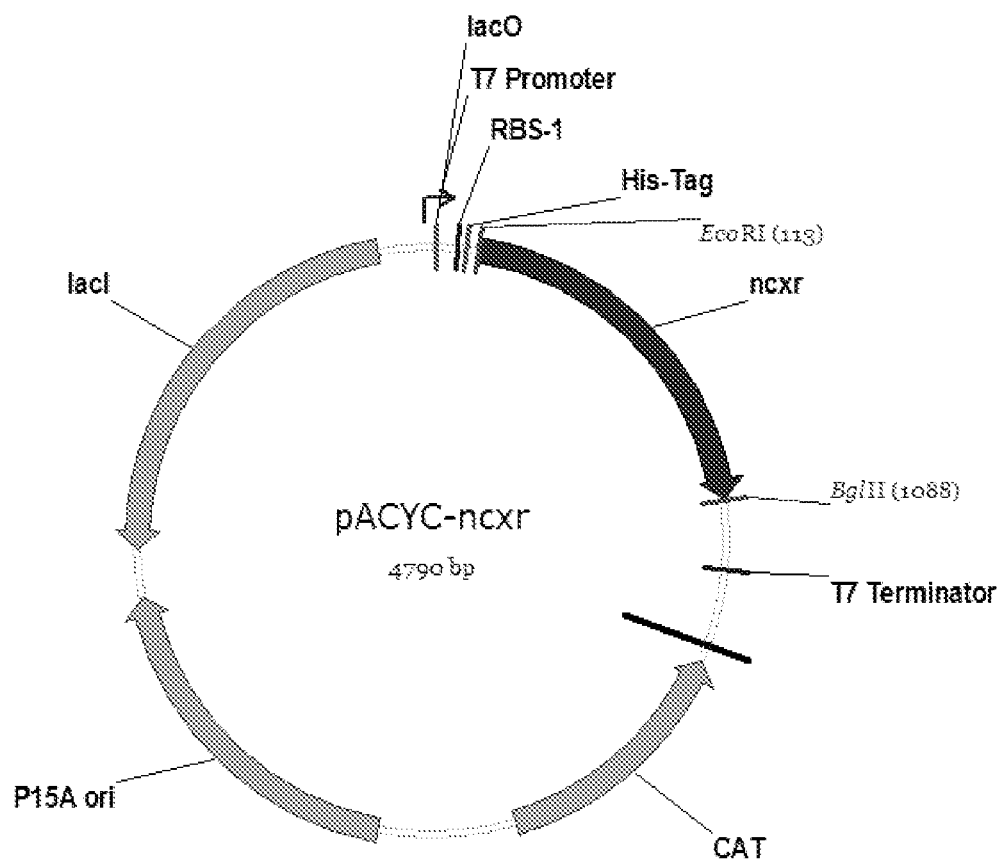
FIG. 3 shows a vector map of pACYC-ncxr.

High levels of soluble expression for NcXR can be achieved in E. coli expression strain BL21 (DE3) under a strong and inducible 17 promoter. However, in order to develop a selection strain to engineer a xylose-specific XR, a vector providing a lower, more physiological-level expression is desirable. Thus plasmids pTrc99A, pKK223-3, pQE-80L, and pMAL-c2x (under trc, tac, T5, and tac promoters, respectively) were tested as expression vectors. The 969 bp gene ncxr PCR amplified from pET15b-ncxr [Woodyer, et al., (2005) Heterologous expression, purification, and characterization of a highly active xylose reductase from Neurospora crassa. Appl Environ Microbiol, 71(3), 1642-7] was cloned into these vectors at various restriction sites within the multiple cloning site (MCS), however, no soluble or insoluble expression in hosts WM1788, XL1-Blue, or JM109 was observed by SDS-PAGE analysis (FIG. 2). The gene was expressed under a T7 promoter of pACYCDuet-1 and pET20b and expressed in BL21 (DE3). Expression using pACYC-ncxr was also tested using the strain WM 1788 (DE3) with positive results. The use of WM1788 (DE3) in conjunction with pACYCDuet-1 expression vector, which while using a T7 promoter, resulted in acceptable expression levels due to a low plasmid copy number. Crude lysate activity assays and sequencing data confirmed active expression and that no incidental mutations had been introduced during cloning steps. The inclusion of a His$_6$-tag (SEQ ID NO: 114) for purification, and tunable expression level based on inducer (IPTG) concentration, as well as a compatible origin of replication with several other vectors made pACYC-ncxr (FIG. 3) an ideal construct for further studies described herein. However, any vector is suitable for expression as long as the expression level and the activity level of xylose reductase are acceptable.

EXAMPLE 2

High-Throughput Selection Method

An efficient high throughput selection method is required to the success of any directed evolution undertaking. In order to pre-select mutants with promising phenotype among those without, a selection strain was developed that directly correlates substrate specificity of mutant NcXR with survival of the host expressing it.

Figure 4:
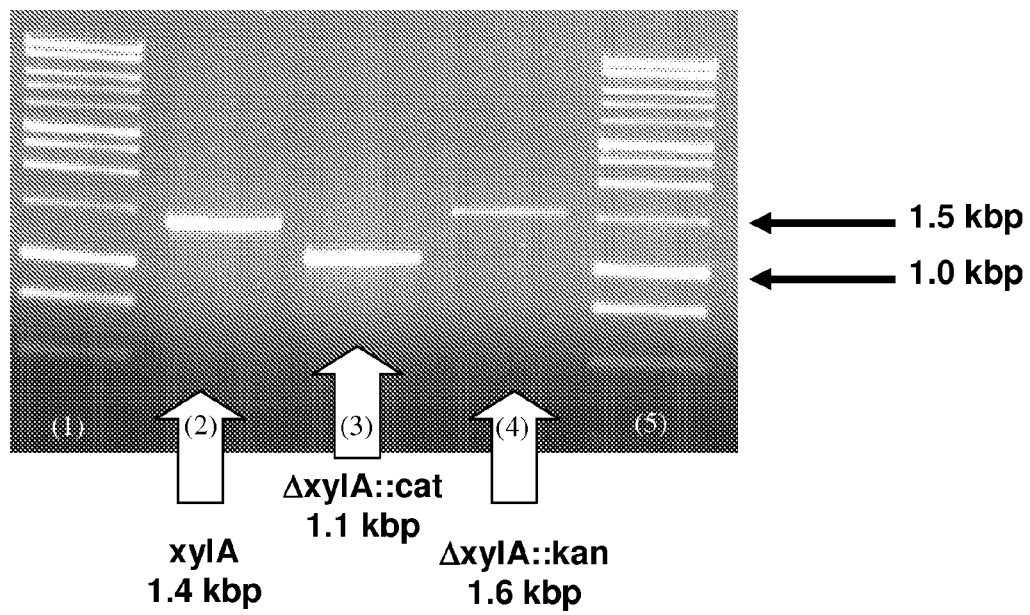
FIG. 4 shows colony PCR products shown on agarose gel confirming replacement of 1.4 kbp xylA gene (lane 2) with either 1.1 kbp cat (lane 3) or 1.6 kbp kan (lane 4) selection markers. DNA ladders (lanes 1 & 5); kbp, kilobasepairs.
Figure 5:
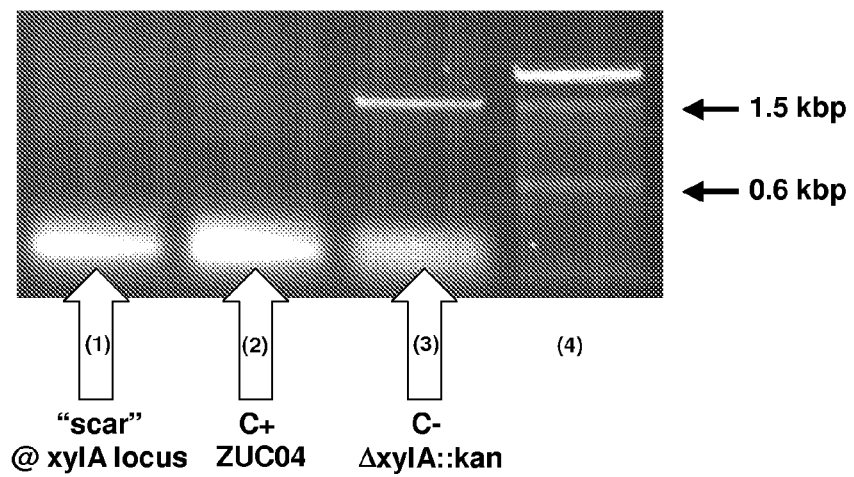
FIG. 5 shows colony PCR product shown on agarose gel confirming deletion of xylA (lane 1), positive control strain ZUC041 (ΔxylA genotype) (lane 2) and negative control strains and WM1788 (DE3) (ΔxylA::kan genotype) (lane 3), respectively. DNA ladder (lane 4); kbp, kilobasepairs.
Figure 6:
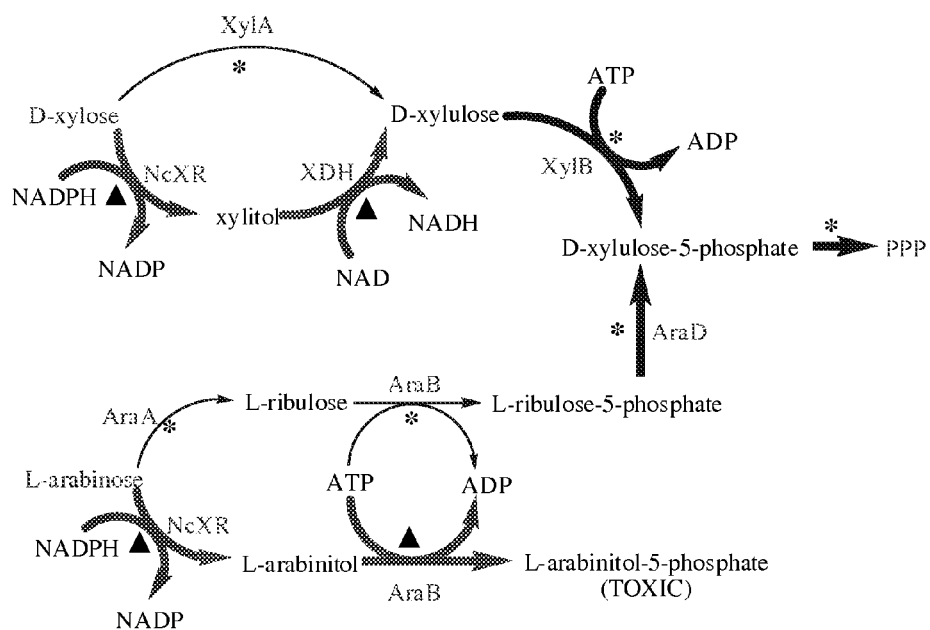
FIG. 6 shows recombinant (triangle) and endogenous (asterisk) pathways in HZ353 catalyzed by various enzymes. Bold arrows indicate pathways, and metabolites are also shown in HZ353.

The first is toxicity due to the synthesis of a lethal phosphorylated intermediate. Second, sugar-specific phosphotransferases in E. coli are known to lack strict substrate specificities, and can therefore be used to generate a toxic phosphorylated sugar-derivative. To implement such a strategy, a shunt was engineered in the pathway for xylose metabolism to link the activity of XR with the ability of the cells to survive on xylose as a sole carbon source. This provided a positive selection selecting only those cells with active NcXR mutants on minimal xylose medium. Next, it was required to generate a phosphorylated intermediate from L-arabinitol, the product of a promiscuous NcXR able to reduce arabinose. This is the negative selection that inhibits growth of cells that encode for a mutant XR with significant activity toward arabinose. Pathway engineering involved inactivating the endogenous xylose isomerase (XyLA) and redirecting carbon flow to NcXR encoded on pACYC-ncxr. Replacement of xylA in WM1788 (DE3) by FRT flanked kan or cat selectable marker (FIG. 4) and subsequent deletion of said markers (FIG. 5) was established using colony PCR. This strain was renamed HZ348. Inactivation of arabinose metabolism pathway was unnecessary since the parental strain WM1788 (DE3) had ΔaraBAD genotype. This genotype was one of the reasons in choosing WM1788 (DE3) as an expression host and not BL21 (DE3), which has an intact arabinose metabolism pathway. The final steps involved completing the xylose metabolism pathway and introducing a sugar-specific phosphotransferase enzyme with poor substrate recognition. Since XR converts xylose into xylitol, a compound that cannot be metabolized by E. coli, a second enzyme xylitol dehydrogenase (XDH) was required to oxidize xylitol into D-xylulose, a ketose that can be easily assimilated into the pentose phosphate pathway. The XDH from Gluconobacter oxydans was chosen for this purpose. The XDH gene sequence for G. oxydans is obtained from GenBank database using accession number AB091690.1 and a stock strain is obtained from ATCC using accession number ATCC 621 [see Sugiyama et al. (2003), Biosci. Biotechnol. Biochem. 67 (3), 584-591, incorporated herein by reference in its entirety]. L-ribulokinase encoded by E. coli araB is a phosphotransferase whose natural substrate is L-ribulose, however due to its promiscuity is able to accept L-arabinitol. These two genes were cloned into a constitutive expression vector pTKXb and introduced into HZ348 to yield HZ349. A summary of pathway engineering including enzymes and intermediates involved are illustrated in FIG. 6.

Growth of HZ353 (HZ349 with pACYC-ncxr) was confirmed on minimal medium with xylose as the only carbon source. Neither HZ348, nor HZ349 grew on xylose medium, confirming that active NcXR is essential for growth. Presence of arabinose in the medium inhibited rate of colony formation significantly, but did not completely prevent growth of HZ353 even at high concentrations. The optimum conditions for cell growth and selection were determining by varying several parameters individually and are summarized in TABLE 3.

EXAMPLE 3

Quantitative Assay for NcXR Activity & Selectivity

The reduction of substrates by XR is accompanied by a concomitant stoichiometric oxidation of NADPH (nicotinamide adenine dinucleotide phosphate, reduced form) cofactor, which has a characteristic absorbance at 340 nm. Therefore, the rate of reaction can be directly monitored as the slope of decreasing absorbance of reaction mixture by a UV/Vis spectrophotometer. This can be performed for purified proteins, and even crude cell lysates with overexpressed XR allowing for adaptation into a higher throughput screen in when used in conjunction with a plate-reader.

A second screen for NcXR activity in a 96-well plate format was developed to determine activity of NcXR and mutants in a more quantitative manner, in presence of D-xylose or L-arabinose. Colonies formed by individual transformants were picked from an agar plate, grown, and induced to express mutant NcXRs. Cell-free lysates were individually tested for activity toward xylose and arabinose with the reaction rate monitored by a spectrophotometric plate-reader. Initial slopes were a measure of activity toward each substrate and a ratio between reaction rate between arabinose and xylose was used as a measure of selectivity. The overall "fitness" (Equation 1) of a mutant was defined as the ratio between its activity (Equation 2) and selectivity (Equation 3).

EQUATIONS $$\text{Fitness} = \frac{A}{S} = \frac{\text{relative Activity toward xylose}}{\text{relative Selectivity toward arabinose}} = \left(\frac{rate_{mutant}}{rate_{parent}}\right)_{xylose} \Big/ \left(\frac{rate_{arabinose}}{rate_{xylose}}\right) \quad \text{Equation 1}$$

$$\text{Relative Selectivity toward arabinose} = \frac{rate_{arabinose}}{rate_{xylose}} \quad \text{Equation 2}$$

$$\text{Relative Activity toward xylose} = \left(\frac{rate_{mutant}}{rate_{parent}}\right)_{xylose} \quad \text{Equation 3}$$

$$CV = \frac{\sigma_x}{\langle x \rangle} \times 100\% \quad \text{Equation 4}$$

To determine the optimum conditions so as to minimize errors, experiments were conducted. Excessive variations in readings would result in false positives or negative results, and therefore it was important to determine conditions under which the coefficient of variance (CV, Equation 4), or deviation from the mean remained under 20%. These conditions were finalized for BL21 (DE3) harboring pACYC-ncxr as well as for HZ353. Cells were picked into 96-well plates and grown till late log-phase at 37° C. and thereafter induced at 30° C. with a high concentration of IPTG for 16-20 hrs. The long induction time allowed the cell density in all wells to reach approximately the same value. Constant shaking was imperative to prevent cells from settling to the bottom and for proper aeration. Microtiter plates were incubated in a humid environment to minimize evaporative losses. Incomplete cell lysis is possible of variation which was avoided by using plate sealers to cover plates and served a dual purpose of enabling high speed vortexing without spillage and also of preventing inter-well contamination. It was noticed that variation was minimized when high reaction rates were measured over a short period of time (1 min), thus also providing a better resolution of relative activities. Substrate concentrations used were near $K_M$ values, also to provide the highest resolution for changes in affinity toward either substrate.

EXAMPLE 4

Determination of Substrate Interacting Residues

To determine residues interacting directly with the substrates, xylose was first docked into the substrate binding pocket of NcXR homology model and was subjected to energy minimization. Due to the promiscuous nature of NcXR, it has a large pocket for binding substrates. Therefore residues with atoms within 8 Å were considered as substrate interacting, instead of 4.5 Å, which is generally considered within van der Waals interaction distance. Thirteen residues were found to be within this distance, and are listed in TABLE 4. A similar docking process was repeated for arabinose, to determine key residue interactions that may discriminate between the two substrates. Functional classification based on docking analysis and available data was performed to identify the minimal subset of residues that can be mutated without significantly inhibiting activity. Other than the residues known to be imperative for catalysis (Tyr49 and Lys78) all residues were considered for mutagenesis. The three residues identified as most important for discriminating between C4-epimers xylose and arabinose were Asp48, Phe112, and Asn307 based on their apparent proximity to the fourth carbon (C4).

EXAMPLE 5

Creating and Screening Mutant Libraries

Several rounds of screening were used to analyze the mutants to minimize the number of false positives from the library. After selection on solid media, colonies were picked and used in 96-well plates and induced cell lysates were used to screen for activity against both xylose and arabinose substrates. Mutants (usually <150) with highest fitness (Equation 1) were streaked on chloramphenicol (Cm) supplemented LB plates and then re-screened as before, but in triplicate, i.e., three colonies were picked and screened per mutant. This round of screening was able to eliminate a large number of false positives since outliers would easily be identified by large deviations from average readings for the mutant. Thereafter, a third round of screening was performed using 1-5 mL cultures grown in tubes instead of 96-well plates. Hereinafter, screening was performed individually on each lysate with either of the substrates using the Cary UVN is spectrophotometer. The number of promising mutants was usually narrowed from ~15 to one or two after this round of screening. Finally, a fourth round of screening was performed using purified protein and the mutants were further characterized to determine its kinetic parameters.

EXAMPLE 6

Kinetic Characterization of Mutant NcXRs

Figure 10:
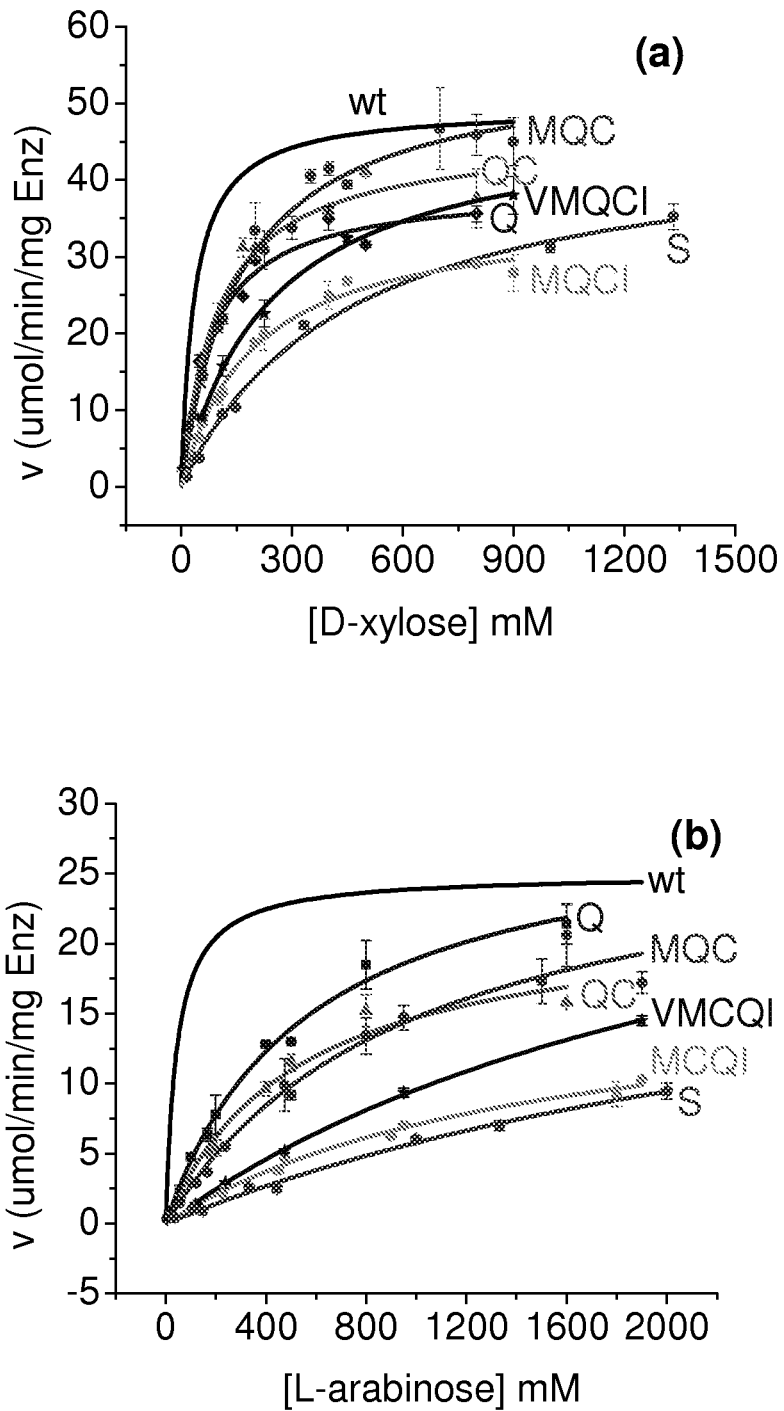
FIG. 10 shows Michaelis-Menten plots for mutant XRs using (a) D-xylose and (b) L-arabinose.

Michaelis-Menten kinetic parameters toward xylose and arabinose were determined for mutant XRs that showed a greater preference for xylose that arabinose. NADPH concentration was kept >100 µM at all times, making it the non-rate-limiting reagent assuming no significant change in $K_M$ for mutants from the 1.8 µM for wild-type NcXR toward NADPH. All reactions were performed at pH 6.3 and 25° C., allowing for easy comparison to published data on wild-type NcXR. Initial reaction rate at each substrate concentration was measured by monitoring the rate of change at $A_{340}$ upon addition of purified enzyme to the substrate mix. All readings were taken in at least two independent two data sets to minimize random error and eliminate experimental artifacts. $His_6$-tag (SEQ ID NO: 114) was not cleaved from the enzyme after purification because its presence does not significantly affect reaction rate. Maximum reaction rates ($k_{cat}$) were calculated based on molecular weight of dimeric NcXR. The Michaelis-Menten parameters for mutants from each round of mutagenesis are summarized in FIG. 10 and TABLE 5.

EXAMPLE 7

Substrate and Product Inhibition

Chemical reactions generally proceed at quicker rates when reactants are present at high concentrations. In certain cases high concentrations of substrates or products can reduce the activity of enzymes, thus lowering the yield of processes. While this is not quite as important for fermentation studies where transport within cells can mitigate inhibitory concentration effects, it may be important in purified enzyme reactors where concentrations can be adjusted to provide maximum yield. Substrate and product inhibition studies can be performed with various substrate concentration and production of xylitol for the mutant xylose reductases described herein.

EXAMPLE 8

Reactor Studies with Mixed Sugars and Production of Ethanol

Reactor studies (either fermentative or purified enzyme-based) are performed with the mutant xylose reductases described herein that specifically reduce xylose to xylitol in a mixture of several sugars, or a mixture of xylose and arabinose.

Xylose is converted into xylitol by XR, which is subsequently converted into ethanol by xylitol dehydrogenase, (for xylitol dehydrogenase, see U.S. Pat. No. 6,582,944, which is incorporated herein by reference in its entirety).

Suitable heterologous hosts include yeast, bacteria and plant cells engineered to express the mutant xylose reductases from *N. crassa* disclosed herein. Other enzyme components such as xylitol dehydrogenase or any other necessary enzymes needed for the production of ethanol or xylitol can also be engineered in the heterologous hosts.

EXAMPLE 9

Enzyme Stability Studies

Thermostability of the XR mutants is tested at production conditions. While temperature is limited at 30 to 37° C. for fermentation processes involving *S. cerevisiae* or *E. coli*, purified enzyme reactors can be operated at higher temperatures, provided the enzyme are sufficiently stable. Since reaction rates increase with temperature, elevated reaction temperatures may result in higher yielding processes. The thermostability of the xylose reductase mutants described herein may be improved by further engineering of amino acid substitutions. Suitable temperatures include for example, 40-45° C., 45-55° C., and 50-60° C.

EXAMPLE 10

Biomass Fermentations

Xylose utilization is desirable for the economic feasibility of biomass fermentations. Although a few xylose-fermenting yeasts are found in nature, *S. cerevisiae* is used ubiquitously for industrial ethanol production. Because *S. cerevisiae* cannot assimilate xylose, attempts to develop a strain of *S. cerevisiae* capable of using xylose have focused on adapting the xylose metabolic pathway from the xylose-utilizing yeasts, such as *Pichia stipitis*. In *Pichia stipitis*, conversion of xylose to xylulose is catalyzed by two oxidoreductases. Xylose is reduced to xylitol by an $NAD[P]H^+$ linked xylose reductase (XR), and the xylitol is oxidized to xylulose by an $NAD^+$ linked xylitol dehydrogenase (XDH). D-xylulokinase (XK) phosphorylates D-xylulose to form D-xyluose-5-phosphate (X5P), which is metabolized further via the pentose phosphate pathway (PPP) and glycolysis.

Suitably, the recombinant microbial strains are able to grow under conditions similar to those found in industrial sources of xylose. The xylose-containing material can be inoculated with a suitable recombinant strain without excessive manipulation. By way of example, the pulping industry generates large amounts of cellulosic waste. Saccharification of the cellulose by acid hydrolysis yields hexoses and pentoses that can be used in fermentation reactions.

By "xylose-containing material," it is meant any medium comprising xylose, whether liquid or solid. Suitable xylose-containing materials include, but are not limited to, hydrolysates of polysaccharide or lignocellulosic biomass such as corn hulls, wood, paper, agricultural by-products, and the like.

Materials and Methods

Strains, Plasmids and Reagents

Expression vector plasmids pET20b and pACYCDeut-1 were obtained from Novagen (San Diego, Calif.), pTrc99A and pKK223-3 from Amersham Biosciences (Piscataway, N.J.), pMAL-c2x from New England Biolabs (NEB, Beverly, Mass.), pQE-80L from Qiagen (Valencia, Calif.), and p6xHTKXb119 was from postdoctoral resident Dr. Jungkul Lee (University of Illinois, Urbana, Ill.). Plasmids for *E. coli* gene inactivation—pKD46, pKD4, and pCP20 were from Dr. Barry L. Wanner (Purdue University, West Lafayette, Ind.). DNA primers were synthesized by Integrated DNA Technologies (IDT, Skokie, Ill.). All enzymes used for cloning were bought from NEB (Beverly, Mass.) unless otherwise noted. QIAprep Spin Plasmid Mini-prep Kits, QIAquick PCR Purification and Gel Extraction Kits were purchased from Qiagen (Valencia, Calif.). Wizard Genomic DNA Purification Kit was obtained from Promega (Madison, Wis.). BD TALON Metal Affinity Resin was purchased from Clontech Laboratories, Inc. (Mountain View, Calif.). *E. coli* strains XL1-Blue, JM109 and BL21 (DE3) were from Stratagene (La Jolla, Calif.), DH5α from ZymoResearch (Orange, Calif.), and WM1788 was from Dr. William Metcalf (University of Illinois, Urbana, Ill.). WM1788 (DE3) was from gradate student Ryan Sullivan (University of Illinois, Urbana, Ill.). *Gluconobacter oxydans* (*Acetobacter suboxydans*) ATCC 621 was procured from USDA Agricultural Research Service (Peoria, Ill.). All chemicals were purchased from Sigma (St. Louis, Mo.), except NADPH was also purchased from Jülich Chiral Solutions (Jülich, Germany) and growth media from BD Biosciences (San Jose, Calif.). DNA standards for agarose gel electrophoresis and protein standards for SDS-PAGE were purchased from Bio-Rad (Hercules, Calif.).

Polymerase Chain Reactions (PCR)

TABLE 6 summarizes the DNA primers used for cloning, mutagenesis and gene inactivation using PCR products. Purified genomic DNA or plasmid DNA was used as template in all cases. Typical amplification reactions were performed in a total volume of 100 µl and contained 1×Taq polymerase buffer supplemented with 1.5 mM $Mg^{2+}$, 0.625 µM of each of forward and reverse primers, 0.2 mM each dNTP, 0.75 U Pfu Turbo DNA polymerase and 0.5 U Taq DNA polymerase. Later, the use of Taq/Pfu mix was replaced by 1 U Phusion DNA polymerase, which also used its own HF buffer. When genomic DNA was used as a template, 0.25 µl of genomic DNA solution was added to the PCR reaction. While when a plasmid was used, 20-100 ng was used as template. An MJ Research PTC200 (Bio-Rad, Hercules, Calif.) was used to perform thermal cycling. A typical PCR amplification using Taq/Pfu consisted of an initial denaturation step of 3:30 min at 94° C., followed by 19 cycles of 45 s of denaturation at 94° C., annealing for 30 s at 55° C., and extension for 60 s at 72° C., and then a final elongation step of 5 min at 72° C. When using Phusion DNA polymerase, initial denaturation step at 98° C. for 30 s was followed by 19 cycles of 10 s denaturation at 98° C., annealing for 10 s at 55° C., and extension for 20 s at 72° C., and a final elongation step also at 72° C. for 5 min. Exact parameters varied depending on gene size, GC-content and primer melting temperatures. All PCR products were purified using a QIAquick PCR Purification Kit and stored at −20° C.

SDS-PAGE Analysis

Powerpac 300 power supply, Mini-PROTEAN 3 assembly, sodium dodecyl sulfate (SDS), and pre-cast 15% or 4-20% gradient polyacrylamide gels were purchased from Bio-Rad (Hercules, Calif.). Varying amounts of samples, dependent upon protein concentration, were mixed with 4 µL, 5×SDS-PAGE loading buffer (30% glycerol, 1% SDS, 3% β-mercaptoethanol, 0.3% bromophenol blue, 0.5 M Tris-HCl, pH 6.8) and ddH$_2$O to a final volume of 20 µL. Samples were denatured at 100° C. for 5-10 min, cooled to 4° C., and then loaded onto the gel in a Bio-Rad Mini-PROTEAN 3 assembly. Voltage was supplied by a Bio-Rad Powerpac 300 at a current of 140 V for 70 minutes. Gels were stained by Coomassie Blue with microwave heating at high power for 50 seconds and then allowed to cool to room temperature before destaining 3 hours in 40% methanol and 10% glacial acetic acid solution. Destained gels were scanned and subsequently discarded.

DNA Sequencing

All DNA samples were submitted for sequencing to the Biotechnology Center Core DNA Sequencing Laboratory at the University of Illinois at Urbana-Champaign (Urbana, Ill.). Sequencing reactions were performed as per their instructions.

Cloning and Heterologously Expressing NcXR

Using pET15b-ncXR as template, ncxr gene was PCR amplified between EcoRI/HindIII restriction sites, ligated into pTrc99A and pKK223-3, and electroporated into competent WM1788 cells. Individual colony forming units were grown to mid log-phase in LB medium supplemented with the appropriate antibiotic at 37° C. and induced with 0.5 mM IPTG for 16 to 20 hours at 25° C. Cell lysates were tested for activity and checked for soluble expression by SDS-PAGE. Since no soluble expression was observed, purified plasmids, pTrc99A-ncxr and pKK223-3-ncxr, were electroporated into competent XL1-Blue and JM109 cells and tested for expression, albeit to similar results. The ncxr gene was then re-amplified and cloned between NdeI/HindIII sites, and EcoRI/HindIII sites in pMAL-c2x and also between SphI/HindIII sites in pQE-80L, and electroporated into, and then expressed in WM1788—all with similar results. NcXR was successfully expressed using the aforementioned protocol in pET20b (between NdeI/HindIII) and pACYCDuet-1 (between EcoRI/BglII to incorporate N-terminal $His_6$-tag) (SEQ ID NO: 114) in BL21 (DE3), WM1788 (DE3), and HZ353.

NcXR Cell Lysate Activity Assay

Cells induced to express NcXR were centrifuged, decanted and resuspended in 100 µL/(mL culture) 10 mM MOPS pH 7.2 supplemented with 1 mg/mL Lysozyme. They were then freeze/thawed at −80° C. and 30° C., respectively, to enhance lysis action and finally centrifuged to remove cell debris and maintained on ice to minimize protease activity. Since reduction of xylose or arabinose is accompanied by concomitant oxidation of co-factor NADPH in 1:1 stoichiometric ratio, rate of reaction can be measured as a function of oxidation rate of NADPH into NADP. Reaction rates were measured at 25° C. with 100-400 µM NADPH, 5-1000 mM D-xylose or 5-2000 mM L-arabinose in 50 mM MOPS at pH 6.3 for all assays. Substrate solutions were maintained at 25° C. using a water bath and reaction cuvettes were also maintained at the same temperature using a UV/Vis spectrophotometer with a re-circulating water jacket. Cell lysate supernatant was added directly to 0.5 mL substrate solution, mixed, and decrease in A was measured as a function of time. Initial reaction rate was calculated by using a linear fit between 0.05 min and 0.25 min.

Selection Strain Construction

WM1788 (DE3) (Δ(araBAD)567 ΔlacZ4787 lacI$^q$ rrnB-3 Δ(rhaBAD)568 hsdR514 ΔphoBR580 galU95 recA ΔendA9 (DE3) uidA(ΔMluI)::pir(wt)) was used as background for construction of a xylose-specific XR selection strain (HZ348). Inactivation of xylA was performed as described (Datsenko & Wanner, One-step inactivation of chromosomal genes in *Escherichia coli* K-12 using PCR products. *Proc Natl Acad Sci USA*, 97(12), 6640-5, 2000) with slight modifications. Briefly, expression of λ Red genes (α, β, γ) was induced with 10 mM L-arabinose for 2 hrs in mid-log-phase WM1788 (DE3) pKD46 grown in 2YT media at 30° C., which were then concentrated and made electrocompetent. 2-3 µg PCR product was electroporated into these cells and recovered at 30° C. in SOC medium with 10 mM L-arabinose for 2 hrs before selection on 10 µg/mL Km or 6 µg/mL Cm LB plates at 42° C. PCR product consisted of 40 bp homologous to region flanking xylA in the target chromosome at either ends of an FRT/kan or FRT/cat cassette, as amplified from pKD4 or pKD3 (see TABLE 6 for primer sequences). Substitution of xylA with resistance marker kan or cat was confirmed using several colony PCRs with primers annealing at various positions inside and outside the cassette, and was subsequently excised using temperature induced expression of FLP-recombinase encoded by pCP20 and screened for simultaneous loss of antibiotic marker and helper plasmid at 42° C. Several colony PCRs with primers annealing inside and outside the cassette were used to confirm loss of kan or cat. Loss of helper plasmid pCP20 was confirmed by testing for loss of Amp resistance, as well as lack of plasmid bands on an agarose gel after plasmid isolation. Next, PCR was used to amplify xdh (from *G. oxydans*) and araB (from *E. coli* DH5α) from chromosomal DNA isolated using WIZARD Genomic DNA Purification Kit. An NdeI restriction site was silently mutated from araB (renamed araB') and then spliced together with xdh, both using overlap-extension PCR (OE-PCR), with a ribosomal binding site (rbs) in between to create an xdharaB' construct. This was subsequently cloned at NdeI/XhoI sites in both pTKXb and pET20b. Finally, HZ348 was transformed with pTKXb-xdharaB' and pET20b-xdharaB' to give HZ349 and HZ350, respectively.

Determining Selection Conditions

Selection media consisted of minimal media agar plates with D-xylose as the carbon source, two antibiotics for maintenance of the two plasmids, IPTG for induction of NcXR, and L-arabinose as selection pressure. IPTG concentration was varied between 0 and 0.5 mM, to find the concentration that gave highest growth rate. To verify positive selection, strains lacking NcXR, those with inactive NcXR (D44A and W21A), and those lacking NcXR, XDH and AraB were plated on minimal media without selection pressure or antibiotics to test for non-specific growth. For negative selection, L-arabinose concentration was varied between 0 and 1.0%, to identify sufficient growth pressure to significantly inhibit growth of cells with wild-type NcXR at 37° C. or 30° C. for 7-10 days. Kan and Cam concentrations were tested between 5 μg/mL and 50 μg/mL, to maintain both plasmids, and minimize non-specific growth and contamination over the extended growth period. After several repetitions, HZ349 gave the most consistent results; hence use of HZ350 was not continued.

Identification of Substrate-Interacting Residues

Figure 7:
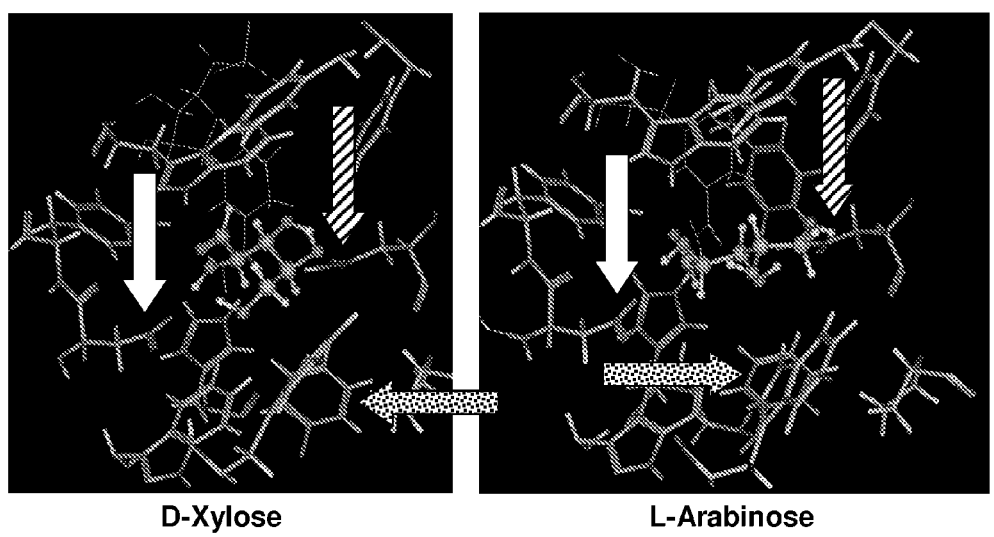
FIG. 7 illustrates substrates docked into the active site of NcXR. The three most important residues identified near C4 for xylose-arabinose discrimination are indicated by arrows in white (Asp48), dotted (Phe112) and striped (Asn307).

Substrate contacting residues and catalytic residues for several aldose reductases (ADRs), including XRs, and the closely related hydroxysteroid dehydrogenase were identified. Corresponding residues were identified in NcXR by multiple sequence alignment (MSA) with human Aldose Reductase (hAR) and rat liver 3α-hydroxysteroid dehydrogenase (3α-HSD). D-xylose was then positioned in the active site of NcXR homology model docked with NADPH (FIG. 7), in Molecular Operating Environment (MOE), with the carbonyl group near the catalytic Tyr49, soaked in water, and subjected to iterative docking. The lowest total energy position was chosen and subjected to further energy minimization. Residues within 8 Å of substrate in the lowest energy configuration were identified as first-shell, substrate-interacting residues. A similar procedure was also used to dock L-arabinose.

His$_6$-tagged (SEQ ID NO: 114) NcXR Purification

Mid-log phase cells with ncxr in expression vector grown in rich media induced with 0.5 mM IPTG for 16-20 hr at 30° C., centrifuged, decanted and the cell pellet re-suspended in 3 mL/(g pellet) 1 mg/mL Lysozyme Wash/Lysis Buffer (50 mM NaH$_2$PO$_4$, 10 mM Imidazole, 15% glycerol, 300 mM NaCl, pH 8.0). They were freeze-thawed twice at −80° C. and 30° C., and then sonicated in 5 s intervals with 10 s pauses for a total of 1 min. To remove cell debris, lysates were centrifuged and the supernatant filtered through 0.22 μm syringe-filters. After equilibrating BD TALON Metal Affinity Resin in columns with 10 column volumes (CV) Wash/Lysis Buffer, cell extracts were loaded and subsequently washed with 10 CV Wash/Lysis Buffer. The columns were eluted with 2-4 CV Elution Buffer (50 mM NaH$_2$PO$_4$, 300 mM Imidazole, 15% glycerol, 300 mM NaCl, pH 8.0) and then regenerated using 1-3 CV of each 0.1 M EDTA/1 M NaCl, 1 N NaOH/1 M NaCl, 1 N HCl, 0.1 M CoCl$_2$, 0.5 M NaCl, and 20% ethanol, with ddH$_2$O in between each step. Eluted proteins were exchanged three times into 10 mM MOPS pH 7.2 using Amicon Ultra-Centrifugal Filter Units (10 or 30 KD MWCO) and concentrated to <1.0 mL. Concentrated enzymes were checked for purity by SDS-PAGE.

Determination of Protein Concentration

Extinction co-efficient for wild-type NcXR was determined and found in agreement with calculated values from San Diego Supercomputing Center (SDSC) Biology Workbench (http://workbench.sdsc.edu/) input with protein sequence. Extinction co-efficient for mutants was thereafter used as calculated by SDSC Biology workbench.

Kinetic Characterization of Mutants

Michaelis-Meten kinetic constants ($K_M$, $k_{cat}$) were determined. All reactions were performed at 25° C. in 50 mM MOPS buffer pH 6.3. NADPH concentration was kept >100 μM, usually between 100-400 μM and substrate concentrations were between 5 and 1500 mM for xylose and between 5 and 2000 mM for arabinose. Purified enzymes were kept on ice at all times to minimize thermal inactivation. Calculations were based on at least two independent datasets of two readings each, and were performed by least-squares fit method in Microcal Origin 5.0 (OriginLab Corporation, Northampton, Mass.). Substrate solutions were maintained at 25° C. in ThermoNESLAB RTE7 refrigerated water bath (Thermo Electron Corporation, Waltham, Mass.). A water-circulating jacketed the cuvette holder in Varian Cary 100 Bio UV-visible spectrophotometer (Varian, Palo Alto, Calif.). 500 μL substrate solution was added to a quartz cuvette with 10 mm path-length and mixed with 0.3-2 μg purified enzyme. Reaction rate was monitored as decrease in absorbance at 340 nm, corresponding to oxidation of NADPH (c=6220 $M^{-1}$ $cm^{-1}$) to NADP. Initial reaction rate was measured as the slope between 0.05 min and 0.25 min. Specific activity calculated for various substrate concentrations from initial reaction rates was used to calculate Michaelis-Menten constants.

Library Creation and Screening

Saturation mutagenesis libraries were created using splicing overlap-extension PCR (OLE-PCR) using NNS primers (TABLE 6). Two fragments of mutant ncxr gene were amplified using standard protocols and spliced together thereafter. 1:1 molar ratio of each fragment was mixed in a 20 μL reaction mix and amplified without primers using a slightly modified PCR reaction, with only 9 cycles of amplification to yield full-length genes. The remaining conditions were maintained as for any other PCR reaction. 0.4-0.5 μL amplicons were used as template for further amplification using end-primers. Products were PCR purified and stored at −20° C. EpPCR library inserts were created using 0.2 mM $Mn^{2+}$ and Tag polymerase with 10 ng plasmid DNA as template, as per standard protocols. Inserts were subsequently PCR purified and stored at −20° C. All inserts were ligated into vectors and electroporated into competent cells. After recovery, HZ349 were washed thoroughly in M9 salt solution and plated on selection media or resuspended in liquid selection media, whereas BL21 (DE3) were spread on LB plates supplemented with 25 μg/mL Cm. Transformed HZ349 grown in liquid medium were incubated for 6 days and their plasmid isolated and transformed into BL21 (DE3) cells and subsequently selected on Cm LB plates. Individual colonies were picked into 100 μL LB media 96-well plates and incubated at 37° C. till late-log-phase and induced with an additional 100 μL LB and 1.0 mM IPTG for 16-20 hrs at 30° C. Plates were centrifuged and resuspended in 1 mg/mL Lysozyme solution in 10 mM MOPS pH 7.2, vortexed and freeze-thawed to complete lysis. 10-20 μL lysate was used in a cell-lysate-based activity assay, as previously discussed using a plate-reader measuring decreasing in $A_{340}$. Relative activities and selectivities were calculated (Equation 2, Equation 3) and promising mutants were further scrutinized using a second 96-well-plate based assay with each mutant represented in triplicate, and thereafter in tube-culture lysate-based and purified enzyme-based activity assays.

Amino acid sequence of *N. crassa* xylose reductase, also designated as NCU 08384.1 (gb|EAA34695.1|) by NCBI:

(SEQ ID NO: 1)

```
  1 MVPAIKLNSG FDMPQVGFGL WKVDGSIASD VVYNAIKAGY RLFDGACDYG NEVECGQGVA

61 RAIKEGIVKR EELFIVSKLW NTFHDGDRVE PIVRKQLADW GLEYFDLYLI HFPVALEYVD

121 PSVRYPPGWH FDGKSEIRPS KATIQETWTA MESLVEKGLS KSIGVSNFQA QLLYDLLRYA

181 KVRPATLQIE HHPYLVQQNL LNLAKAEGIA VTAYSSFGPA SFREFNMEHA QKLQPLLEDP

241 TIKAIGDKYN KDPAQVLLRW ATQRGLAIIP KSSREATMKS NLNSLDFDLS EEDIKTISGF

301 DRGIRFNQPT NYFSAENLWI FG.
``` cDNA sequence of *N. crassa* xylose reductase:

(SEQ ID NO: 2)

```
  1 atggttcctg ctatcaagct caactccggc ttcgacatgc ccaggtcgg cttcggcctc 61 tggaaggtcg acggctccat cgcttccgat gtcgtctaca acgctatcaa ggcaggctac 121 cgcctcttcg atggtgcctg cgactacggc aacgaggttg agtgcggcca gggtgtagcc 181 cgcgccatca aggagggcat cgtcaagcgc gaggagctct tcatcgtctc caagctctgg 241 aacaccttcc acgacggcga ccgcgtcgag cccatcgtcc gcaagcagct tgccgactgg 301 ggtctcgagt acttcgatct ctacctgatc cacttccccg tcgccctcga gtacgtcgac 361 ccctcggtcc gctaccctcc cggctggcac tttgatggca agagcgagat ccgcccctca 421 aaggccacca tccaagagac ctggacggcc atggagtcgc tcgtcgagaa gggtctctcc 481 aagagcattg gcgtctccaa cttccaggcc cagctcctgt acgacctcct gcgctacgcc 541 aaggtccgcc ccgccactct ccagatcgag caccacccct acctcgtcca gcagaacctc 601 ctcaaccttg ccaaggctga gggcatcgcc gtgaccgcct actcctcctt cggccctgct 661 tctttccgcg agttcaacat ggagcacgcc cagaagctcc agcctctcct cgaggacccc 721 accatcaagg ctattggtga caagtacaac aaggatcctg cccaggtcct cctccgttgg 781 gccacccagc gcggcctggc catcatcccc aagtctagcc gcgaggccac catgaagtcc 841 aacctcaact ctcttgattt cgatctctcc gaggaggaca tcaagaccat ctctggtttc 901 gaccgcggca tccgcttcaa ccagcccacc aactacttct ccgctgagaa cctctggatt 961 ttcggttag.
```

Sequence for VMQCI:

(SEQ ID NO: 115)

```
Atggttcctgctatcaagctcaactccggcttcgacatgccccaggtcggcttcggcctctggaaggtcga cggctccatcgcttccgatgtcgtctacaacgctatcaaggcaggctaccgcctcttcgatggtgcctgcg actacggcaacgaggttgagtgcggccagggtgtagcccgcgccatcaaggagggcatcgtcaagcgcgag gagctctttatcgtctccaagctctggaacaccttccacgacggcgaccgcgtcgagcccatcgtccgcaa gcagcttgccgactggggtgtggagtacttcgatatgtaccagtgccacttccccatcgccctcgagtacg tcgaccccctcggtccgttaccctcccggctggcactttgacggcaagagcgagatccgcccctccaaggcc accatccaagagacctggacggccatggagtcgctcgtcgagaagggtctctccaagagcattggcgtctc caacttccaggcccagctcctgtacgacctcctccgctacgccaaggtccgccccgccactctccagatcg agcaccaccctacctcgtccagcagaacctcctcaaccttgccaaggctgagggcatcgccgtgaccgcc tactcctccttcggccctgcttctttccgcgagttcaacatggagcacgcccagaagctccagcctctcct
```

-continued

```
cgaggaccccaccatcaaggctattggtgacaagtacaacaaggatcctgcccaggtcctcctccgttggg ccacccagcgcggcctggccatcatccccaagtctagccgcgaggccaccatgaagtccaacctcaactct cttgatttcgatctctccgaggaggacatcaagaccatctctggtttcgaccgcggcatccgcttcaacca gcccaccaactacttctccgccgagaacctctggattttcggttag
```

Sequence for S:

(SEQ ID NO: 116)
```
atggttcctgctatcaagctcaactccggcttcgacatgccccaggtcggcttcggcctctggaaggtcga cggctccatcgcttccgatgtcgtctacaacgctatcaaggcaggctaccgcctcttcgatggtgcctgcg actacggcaacgaggttgagtgcggccagggtgtagcccgcgccatcaaggagggcatcgtcaagcgcgag gagctctttatcgtctccaagctctggaacaccttccacgacggcgaccgcgtcgagcccatcgtccgcaa gcagcttgccgactggggtctcgagtacttcgatctctacctgatccactcgcccgtcgccctcgagtacg tcgaccctcggtccgttaccctcccggctggcactttgacggcaagagcgagatccgcccctccaaggcc accatccaagagcctggacggccatggagtcgctcgtcgagaagggtctctccaagagcattggcgtctc caacttccaggcccagctcctgtacgacctcctccgctacgccaaggtccgccccgccactctccagatcg agcaccaccctacctcgtccagcagaacctcctcaaccttgccaaggctgagggcatcgccgtgaccgcc tactcctccttcggccctgcttctttccgcgagttcaacatggagcacgcccagaagctccagcctctcct cgaggaccccaccatcaaggctattggtgacaagtacaacaaggatcctgcccaggtcctcctccgttggg ccacccagcgcggcctggccatcatccccaagtctagccgcgaggccaccatgaagtccaacctcaactct cttgatttcgatctctccgaggaggacatcaagaccatctctggtttcgaccgcggcatccgcttcaacca gcccaccaactacttctccgctgagaacctctggattttcggttag
```

TABLE 1

Comparison of XRs from various organisms.

| Organism | $k_{cat}$ (min$^{-1}$) | $K_{M, xylose}$ (mM) | $k_{cat}/K_{M, xylose}$ (mM$^{-1}$min$^{-1}$) | $K_{M, NADPH}$ (μM) | $k_{cat}/K_{M, NADPH}$ (μM$^{-1}$min$^{-1}$) |
|---|---|---|---|---|---|
| N. crassa | 3600 | 34 | 106 | 1.8 | 2000 |
| C. intermedia | 900 | 50 | 18 | 56 | 16 |
| C. parapsilosis | 3100 | 32 | 98 | 37 | 84 |
| C. tropicalis | ND | 30-37 | ND | 9-18 | ND |
| C. tenuis | 1300 | 72 | 18 | 4.8 | 271 |
| P. tannophilus | 600 | 162 | 4 | 59 | 10 |
| P. siptitus | 1500 | 42 | 36 | 9 | 167 |
| S. cerevisiae | 860 | 13.6 | 63 | 7.6 | 113 |

TABLE 2

Substrate specificity of N. crassa XR.

| Substrate | $k_{cat}$ (min$^{-1}$) | $K_M$ (mM) | $k_{cat}/K_M$ (mM$^{-1}$min$^{-1}$) | Efficiency |
|---|---|---|---|---|
| D-xylose | 3600 ± 200 | 34 ± 4 | 110 | 100% |
| D-ribose | 3120 ± 100 | 70 ± 10 | 45 | 41% |
| L-arabinose | 1800 ± 100 | 40 ± 10 | 45 | 41% |
| D-galactose | 1800 ± 100 | 180 ± 30 | 10 | 9% |
| D-glucose | 1320 ± 100 | 360 ± 60 | 3.6 | 3% |

TABLE 3

Optimum growth conditions for HZ353. Arabinose used only when applying selective pressure.

| Variable | Optimum |
|---|---|
| Temperature | 30° C. |
| IPTG | 10 μM |
| Thiamine-HCl | 0.001% |
| M9 salts | 1 x |
| MgSO$_4$ | 2 mM |
| CaCl$_2$ | 0.1 mM |
| D-Xylose | 0.50% |
| L-Arabinose | 0.50% |
| Kanamycin (Kn) | 5 μg/mL |
| Chloramphenicol (Cm) | 5 μg/mL |

TABLE 4

List of substrate contacting residues identified by docking analysis. Hypothesized function listed.

| Residue | Hypothesized Function |
| --- | --- |
| Trp21 | Catalytic Activity |
| Asp44 | Catalytic Activity |
| Asp48 | Discrimination between xylose and arabinose |
| Tyr49 | Known Catalytic Residue |
| Lys78 | Known Catalytic Residue |
| Trp80 | Substrate Discrimination |
| His111 | Substrate Discrimination |
| Phe112 | Discrimination between xylose and arabinose |
| Trp129 | Substrate Discrimination |
| Phe222 | Substrate Discrimination |
| Phe225 | Substrate Discrimination |
| Asn307 | Discrimination between xylose and arabinose |
| Pro309 | Substrate Discrimination |

TABLE 5

Summary of kinetic parameters, relative catalytic efficiency, and xylose-to-arabinose selectivity for all mutants.

| Substrate | Mutant | $K_M$ (mM) | ± | $k_{cat}$ (min$^{-1}$) | ± | Catalytic Efficiency | Selectivity |
| --- | --- | --- | --- | --- | --- | --- | --- |
| D-Xylose | wt | 34 | 4 | 3600 | 200 | 100% | 2.4 |
| | Q | 82 | 10 | 2860 | 100 | 33% | 8.9 |
| | QC | 100 | 14 | 3330 | 150 | 31% | 10.8 |
| | MQC | 160 | 15 | 4020 | 125 | 24% | 11.7 |
| | S | 450 | 41 | 3380 | 120 | 7.1% | 13.8 |
| | MQCI | 190 | 20 | 2620 | 100 | 13% | 16.1 |
| | VMQCI | 240 | 18 | 3600 | 123 | 14% | 15.6 |
| L-Arabinose | wt | 40 | 10 | 1800 | 100 | 41% | |
| | Q | 530 | 52 | 2070 | 90 | 3.7% | |
| | QC | 530 | 82 | 1640 | 120 | 2.9% | |
| | MQC | 990 | 210 | 2130 | 210 | 2.0% | |
| | S | 3400 | 800 | 1850 | 310 | 0.51% | |
| | MQCI | 1510 | 210 | 1290 | 100 | 0.81% | |
| | VMQCI | 2600 | 200 | 2500 | 130 | 0.52% | |

TABLE 6

List of primers used. Italics indicate flanking regions, bold indicate restriction sites and plain text indicate template annealing sequence.

| Purpose | Primer Name | Sequence (5' to 3') | SEQ ID NO: |
| --- | --- | --- | --- |
| NcXR cloning | NN_051110_ncXR_EcoRI_fwd | *ATATTA*GAATTCGATGGTTCCTGCTATC | 3 |
| | NN_050613_ncXR_rev_BglII | *TAC*AGATCTCTAACCGAAAATCCAGAG | 4 |
| | NN050223_XR-1 | *TAATGA*GAATTCATGGTTCCTGCTATC | 5 |
| | NN050223_XR-2 | *ATTGCA*AAGCTTCTAACCGAAAATCCAG | 6 |
| | NN050531-ncXR_fwd_SphI | *GATCGGAAC*GCATGCATGGTTCCTGC | 7 |
| | Crassa 1-For NdeI | *GTAGCTACGTCA*CATATGGTTCCTGC | 8 |
| Selection strain construction | NN_050613_xdh_fwd_NdeI | *TCGAAC*CATATGTCGAAGAAGTTTAACGG | 9 |
| | NN_050613_xdh_rev_EcoRV | *GGTATATCTCCTT*GATATCTCAACCGCCAGCAATCGG | 10 |
| | NN_050613_araB_fwd_EcoRV | GATATCAAGGACATATACCATGGCGATTGCAATTGGC | 11 |
| | NN_050613_araB_rev_XhoI | *TCTCTCT*CTCGAGTTATAGAGTCGCAACGGC | 12 |
| | NN_050613_pKD3 + xylA_fwd | *ATATTACGACATCATCCATCACCCGCGGCATTACCTG*ATTGTGTAGGCTGGAGCTGCTTC | 13 |
| | NN_050613_pKD3 + xylA_rev | *TACCGATAACCGGGCCAACGGACTGCACAGTTAGCC*GTTACATATGAATATCCTCCTTAG | 14 |
| | xylA_test_fwd | CGACATCATCCATCACCC | 15 |
| | xylA_test_rev | CGATAACCGGGCCAACGG | 16 |
| Saturation mutagenesis of substrate interacting residues | NN_050928_W21_fwd | GGCTTCGGCCTCNNSAAGGTCGACGGC | 17 |
| | NN_050928_D44_fwd | CTACCGCCTCTTCNNSGGTGCCTGCGAC | 18 |
| | NN_050928_D48_fwd | GATGGTGCCTGCNNSTACGGCAACGAG | 19 |
| | NN_050928_F112_fwd | CTACCTGATCCACNNSCCCGTCGCCCTC | 20 |
| | NN_050928_F225_fwd | CTTCTTTCCGCGAGNNSAACATGGAGCACG | 21 |
| | NN_050928_N307_fwd | GGCATCCGCTTCNNSCAGCCCACCAAC | 22 |
| | NN_050928_W80_fwd | GTCTCCAAGCTCNNSAACACCTTCCAC | 23 |
| | NN_050928_W129_fwd | GTTACCCTCCCGGCNNSCACTTTGACGGC | 24 |
| | NN_050928_P309_fwd | CGCTTCAACCAGNNSACCAACTACTTC | 25 |
| | NN_050928_W21_rev | GCCGTCGACCTTSNNGAGGCCGAAGCC | 26 |
| | NN_050928_D44_rev | GTCGCAGGCACCSNNGAAGAGGCGGTAG | 27 |
| | NN_050928_D48_rev | CTCGTTGCCGTASNNGCAGGCACCATC | 28 |
| | NN_050928_F112_rev | GAGGGCGACGGGSNNGTGGATCAGGTAG | 29 |
| | NN_050928_F225_rev | GCGTGCTCCATGTTSNNCTCGCGGAAAGAAG | 30 |
| | NN_050928_N307_rev | GTTGGTGGGCTGSNNGAAGCGGATGCC | 31 |
| | NN_050928_W80_rev | GTGGAAGGTGTTSNNGAGCTTGGAGAC | 32 |
| | NN_050928_W129_rev | GCCGTCAAAGTGSNNGCCGGGAGGGTAAC | 33 |
| | NN_050928_P309_rev | GAAGTAGTTGGTSNNCTGGTTGAAGCG | 34 |
| Saturation mutagenesis on Q template | NN_XR_L109X_fwd | CGATCTCTACNNSATCCACTCGCC | 35 |
| | NN_XR_L109X_rev | GGCGAGTGGATSNNGTAGAGATCG | 36 |
| | NN_L109Q_I110_fwd | GATCTCTACCAGNNSCACTTCCCCGTC | 37 |
| | NN_L109Q_I110_rev | GACGGGGAAGTGSNNCTGGTAGAGATC | 38 |
| | NN_L109Q_H111_fwd | CTCTACCAGATCNNSTTCCCCGTCGCC | 39 |
| | NN_L109Q_H111_rev | GGCGACGGGGAASNNGATCTGGTAGAG | 40 |

TABLE 6-continued

List of primers used. Italics indicate flanking regions, bold indicate restriction sites and plain text indicate template annealing sequence.

| Purpose | Primer Name | Sequence (5' to 3') | SEQ ID NO: |
|---|---|---|---|
| Saturation mutagenesis on QC template | NN_L109QI110C_D106X_fwd | CTCGAGTACTTCNNSCTCTACCAGTGC | 41 |
| | NN_L109QI110C_L107X_fwd | GAGTACTTCGATNNSTACCAGTGCCAC | 42 |
| | NN_L109QI110C_Y108X_fwd | GTACTTCGATCTCNNSCAGTGCCACTTCC | 43 |
| | NN_L109QI110C_H111X_fwd | CTCTACCAGTGCNNSTTCCCCGTCGCC | 44 |
| | NN_L109QI110C_F112X_fwd | CTACCAGTGCCACNNSCCCGTCGCCCTCG | 45 |
| | NN_L109QI110C_P113X_fwd | CAGTGCCACTTCNNSGTCGCCCTCGAG | 46 |
| | NN_L109QI110C_D106X_rev | GCACTGGTAGAGSNNGAAGTACTCGAG | 47 |
| | NN_L109QI110C_L107X_rev | GTGGCACTGGTASNNATCGAAGTACTC | 48 |
| | NN_L109QI110C_Y108X_rev | GGAAGTGGCACTGSNNGAGATCGAAGTAC | 49 |
| | NN_L109QI110C_H111X_rev | GGCGACGGGGAASNNGCACTGGTAGAG | 50 |
| | NN_L109QI110C—F112X_rev | CGAGGGCGACGGGSNNGTGGCACTGGTAG | 51 |
| | NN_L109QI110C_P113X_rev | CTCGAGGGCGACSNNGAAGTGGCACTG | 52 |
| Saturation mutagenesis on MQC template | NN_XR_M_L102X_fwd | GCCGACTGGGGTNNSGAGTACTTCGATATG | 53 |
| | NN_XR_M_E103X_fwd | GACTGGGGTCTCNNSTACTTCGATATG | 54 |
| | NN_XR_M_Y104X_fwd | CTGGGGTCTCGAGNNSACTTCGATATGTAC | 55 |
| | NN_XR_MQ_F105X_fwd | GGTCTCGAGTACNNSGATATGTACCAG | 56 |
| | NN_XR_MQC_D106X_fwd | CTCGAGTACTTCNNSATGTACCAGTGC | 57 |
| | NN_XR_MQC_Y108X_fwd | GTACTTCGATATGNNSCAGTGCCACTTCC | 58 |
| | NN_XR_MQC_H111X_fwd | GATATGTACCAGTGCNNSTTCCCCGTCGCCCTC | 59 |
| | NN_XR_MQC_F112X_fwd | GTACCAGTGCCACNNSCCCGTCGCCCTC | 60 |
| | NN_XR_A115X_fwd | CACTTCCCCGTCNNSCTCGAGTACGTC | 61 |
| | NN_XR_L116X_fwd | CTTCCCCGTCGCCNNSGAGTACGTCGACC | 62 |
| | NN_XR_E117X_fwd | CCCGTCGCCCTCNNSTACGTCGACCCC | 63 |
| | NN_XR_Y118X_fwd | GTCGCCCTCGAGNNSGTCGACCCCTCG | 64 |
| | NN_XR_M_L102X_rev | CATATCGAAGTACTCSNNACCCCAGTCGGC | 65 |
| | NN_XR_M_E103X_rev | CATATCGAAGTASNNGAGACCCCAGTC | 66 |
| | NN_XR_M_Y104X_rev | GTACATATCGAAGTSNNCTCGAGACCCCAG | 67 |
| | NN_XR_MQ_F105X_rev | CTGGTACATATCSNNGTACTCGAGACC | 68 |
| | NN_XR_MQC_D106X_rev | GCACTGGTACATSNNGAAGTACTCGAG | 69 |
| | NN_XR_MQC_Y108X_rev | GGAAGTGGCACTGSNNCATATCGAAGTAC | 70 |
| | NN_XR_MQC_H111X_rev | GAGGGCGACGGGGAASNNGCACTGGTACATATC | 71 |
| | NN_XR_MQC_F112X_rev | GAGGGCGACGGGSNNGTGGCACTGGTAC | 72 |
| | NN_XR_A115X_rev | GACGTACTCGAGSNNGACGGGGAAGTG | 73 |
| | NN_XR_L116X_rev | GGTCGACGTACTCSNNGGCGACGGGGAAG | 74 |
| | NN_XR_E117X_rev | GGGGTCGACGTASNNGAGGGCGACGGG | 75 |
| | NN_XR_Y118X_rev | CGAGGGGTCGACSNNCTCGAGGGCGAC | 76 |
| | NN_QC_V114X_fwd | GTGCCACTTCCCCNNSGCCCTCGAGTACG | 77 |
| | NN_QC_V114X_rev | CGTACTCGAGGGCSNNGGGGAAGTGGCAC | 78 |
| Saturation mutagenesis on MQCI template | NN_XR_M_L102X_fwd | GCCGACTGGGGTNNSGAGTACTTCGATATG | 79 |
| | NN_XR_M_E103X_fwd | GACTGGGGTCTCNNSTACTTCGATATG | 80 |
| | NN_XR_M_Y104X_fwd | CTGGGGTCTCGAGNNSACTTCGATATGTAC | 81 |
| | NN_XR_MQ_F105X_fwd | GGTCTCGAGTACNNSGATATGTACCAG | 82 |
| | NN_XR_MQC_D106X_fwd | CTCGAGTACTTCNNSATGTACCAGTGC | 83 |
| | NN_XR_MQC_Y108X_fwd | GTACTTCGATATGNNSCAGTGCCACTTCC | 84 |
| | NN_XR_MQC_H111X_fwd | GATATGTACCAGTGCNNSTTCCCCGTCGCCCTC | 85 |
| | NN_XR_MQC_F112X_fwd | GTACCAGTGCCACNNSCCCGTCGCCCTC | 86 |
| | NN_XR_A115X_fwd | CACTTCCCCGTCNNSCTCGAGTACGTC | 87 |
| | NN_XR_L116X_fwd | CTTCCCCGTCGCCNNSGAGTACGTCGACC | 88 |
| | NN_XR_E117X_fwd | CCCGTCGCCCTCNNSTACGTCGACCCC | 89 |
| | NN_XR_Y118X_fwd | GTCGCCCTCGAGNNSGTCGACCCCTCG | 90 |
| | NN_XR_M_L102X_rev | CATATCGAAGTACTCSNNACCCCAGTCGGC | 91 |
| | NN_XR_M_E103X_rev | CATATCGAAGTASNNGAGACCCCAGTC | 92 |
| | NN_XR_M_Y104X_rev | GTACATATCGAAGTSNNCTCGAGACCCCAG | 93 |
| | NN_XR_MQ_F105X_rev | CTGGTACATATCSNNGTACTCGAGACC | 94 |
| | NN_XR_MQC_D106X_rev | GCACTGGTACATSNNGAAGTACTCGAG | 95 |
| | NN_XR_MQC_Y108X_rev | GGAAGTGGCACTGSNNCATATCGAAGTAC | 96 |
| | NN_XR_MQC_H111X_rev | GAGGGCGACGGGGAASNNGCACTGGTACATATC | 97 |
| | NN_XR_MQC_F112X_rev | GAGGGCGACGGGSNNGTGGCACTGGTAC | 98 |
| | NN_XR_A115X_rev | GACGTACTCGAGSNNGACGGGGAAGTG | 99 |
| | NN_XR_L116X_rev | GGTCGACGTACTCSNNGGCGACGGGGAAG | 100 |
| | NN_XR_E117X_rev | GGGGTCGACGTASNNGAGGGCGACGGG | 101 |
| | NN_XR_Y118X_rev | CGAGGGGTCGACSNNCTCGAGGGCGAC | 102 |
| Sequencing primers | NN_051110_ACYCDuetUP1 | GGATCTCGACGCTCTCCCT | 103 |
| | T7 term | GCTAGTTATTGCTCAGCGG | 104 |

The invention claimed is:
1. An engineered nucleic acid molecule comprising a sequence encoding a mutant xylose reductase that has the amino acid sequence of SEQ ID NO:1 with an amino acid substitution of L109Q.

* * * * *

SEQUENCE LISTING

<160> NUMBER OF SEQ ID NOS: 116

<210> SEQ ID NO 1
<211> LENGTH: 322
<212> TYPE: PRT
<213> ORGANISM: Neurospora crassa

<400> SEQUENCE: 1

Met Val Pro Ala Ile Lys Leu Asn Ser Gly Phe Asp Met Pro Gln Val
1               5                   10                  15

Gly Phe Gly Leu Trp Lys Val Asp Gly Ser Ile Ala Ser Asp Val Val
            20                  25                  30

Tyr Asn Ala Ile Lys Ala Gly Tyr Arg Leu Phe Asp Gly Ala Cys Asp
        35                  40                  45

Tyr Gly Asn Glu Val Glu Cys Gly Gln Gly Val Ala Arg Ala Ile Lys
    50                  55                  60

Glu Gly Ile Val Lys Arg Glu Glu Leu Phe Ile Val Ser Lys Leu Trp
65                  70                  75                  80

Asn Thr Phe His Asp Gly Asp Arg Val Glu Pro Ile Val Arg Lys Gln
                85                  90                  95

Leu Ala Asp Trp Gly Leu Glu Tyr Phe Asp Leu Tyr Leu Ile His Phe
            100                 105                 110

Pro Val Ala Leu Glu Tyr Val Asp Pro Ser Val Arg Tyr Pro Pro Gly
        115                 120                 125

Trp His Phe Asp Gly Lys Ser Glu Ile Arg Pro Ser Lys Ala Thr Ile
    130                 135                 140

Gln Glu Thr Trp Thr Ala Met Glu Ser Leu Val Glu Lys Gly Leu Ser
145                 150                 155                 160

Lys Ser Ile Gly Val Ser Asn Phe Gln Ala Gln Leu Leu Tyr Asp Leu
                165                 170                 175

Leu Arg Tyr Ala Lys Val Arg Pro Ala Thr Leu Gln Ile Glu His His
            180                 185                 190

Pro Tyr Leu Val Gln Gln Asn Leu Leu Asn Leu Ala Lys Ala Glu Gly
        195                 200                 205

Ile Ala Val Thr Ala Tyr Ser Ser Phe Gly Pro Ala Ser Phe Arg Glu
    210                 215                 220

Phe Asn Met Glu His Ala Gln Lys Leu Gln Pro Leu Leu Glu Asp Pro
225                 230                 235                 240

Thr Ile Lys Ala Ile Gly Asp Lys Tyr Asn Lys Asp Pro Ala Gln Val
                245                 250                 255

Leu Leu Arg Trp Ala Thr Gln Arg Gly Leu Ala Ile Ile Pro Lys Ser
            260                 265                 270

Ser Arg Glu Ala Thr Met Lys Ser Asn Leu Asn Ser Leu Asp Phe Asp
        275                 280                 285

Leu Ser Glu Glu Asp Ile Lys Thr Ile Ser Gly Phe Asp Arg Gly Ile
    290                 295                 300

Arg Phe Asn Gln Pro Thr Asn Tyr Phe Ser Ala Glu Asn Leu Trp Ile
305                 310                 315                 320

Phe Gly

<210> SEQ ID NO 2
<211> LENGTH: 969
<212> TYPE: DNA
<213> ORGANISM: Neurospora crassa

<400> SEQUENCE: 2

```
atggttcctg ctatcaagct caactccggc ttcgacatgc cccaggtcgg cttcggcctc    60
tggaaggtcg acggctccat cgcttccgat gtcgtctaca acgctatcaa ggcaggctac   120
cgcctcttcg atggtgcctg cgactacggc aacgaggttg agtgcggcca gggtgtagcc   180
cgcgccatca aggagggcat cgtcaagcgc gaggagctct tcatcgtctc caagctctgg   240
aacaccttcc acgacggcga ccgcgtcgag cccatcgtcc gcaagcagct tgccgactgg   300
ggtctcgagt acttcgatct ctacctgatc cacttccccg tcgccctcga gtacgtcgac   360
ccctcggtcc gctaccctcc cggctggcac tttgatggca agagcgagat ccgcccctca   420
aaggccacca tccaagagac ctggacggcc atggagtcgc tcgtcgagaa gggtctctcc   480
aagagcattg gcgtctccaa cttccaggcc cagctcctgt acgacctcct gcgctacgcc   540
aaggtccgcc ccgccactct ccagatcgag caccacccct acctcgtcca gcagaacctc   600
ctcaaccttg ccaaggctga gggcatcgcc gtgaccgcct actcctcctt cggccctgct   660
tctttccgcg agttcaacat ggagcacgcc cagaagctcc agcctctcct cgaggacccc   720
accatcaagg ctattggtga caagtacaac aaggatcctg cccaggtcct cctccgttgg   780
gccacccagc gcggcctggc catcatcccc aagtctagcc gcgaggccac catgaagtcc   840
aacctcaact ctcttgattt cgatctctcc gaggaggaca tcaagaccat ctctggtttc   900
gaccgcggca tccgcttcaa ccagcccacc aactacttct ccgctgagaa cctctggatt   960
ttcggttag                                                           969

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
atattagaat tcgatggttc ctgctatc                                       28

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tacagatctc taaccgaaaa tccagag                                        27

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
taatgagaat tcatggttcc tgctatc                                        27

<210> SEQ ID NO 6
<211> LENGTH: 28
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 6
attgcaaagc ttctaaccga aaatccag                                          28

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gatcggaacg catgcatggt tcctgc                                            26

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gtagctacgt cacatatggt tcctgc                                            26

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tcgaaccata tgtcgaagaa gtttaacgg                                         29

<210> SEQ ID NO 10
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggtatatctc cttgatatct caaccgccag caatcgg                                37

<210> SEQ ID NO 11
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gatatcaagg acatatacca tggcgattgc aattggc                                37

<210> SEQ ID NO 12
<211> LENGTH: 31
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 12
tctctctctc gagttataga gtcgcaacgg c                                    31

<210> SEQ ID NO 13
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
atattacgac atcatccatc acccgcggca ttacctgatt gtgtaggctg gagctgcttc     60

<210> SEQ ID NO 14
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
taccgataac cgggccaacg gactgcacag ttagccgtta catatgaata tcctccttag     60

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cgacatcatc catcaccc                                                   18

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cgataaccgg gccaacgg                                                   18

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (13)..(14)
<223> OTHER INFORMATION: a, c, g, t, unknown, or other

<400> SEQUENCE: 17
ggcttcggcc tcnnsaaggt cgacggc                                         27

<210> SEQ ID NO 18
<211> LENGTH: 28

```
<212> TYPE: DNA
<213> ORGANISM: Artificial Sequence
<220> FEATURE:
<223> OTHER INFORMATION: Description of Artificial Sequence: Synthetic
      primer
<220> FEATURE
<221> NAME/KEY: modified_base
<222> LOCATION: (14)..(15)
<223> OTHER INFORMATION: a, c, g, t, unknown, or other

<400> SEQUENCE: 18
ctaccgcctc ttcnnsggtg cctgcgac                                            28

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (13)..(14)
<223> OTHER INFORMATION: a, c, g, t, unknown, or other

<400> SEQUENCE: 19
gatggtgcct gcnnstacgg caacgag                                             27

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(15)
<223> OTHER INFORMATION: a, c, g, t, unknown, or other

<400> SEQUENCE: 20
ctacctgatc cacnnscccg tcgccctc                                            28

<210> SEQ ID NO 21
<211> LENGTH: 31
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (15)..(16)
<223> OTHER INFORMATION: a, c, g, t, unknown, or other

<400> SEQUENCE: 21
cttctttccg cgagnnsaac atggagcacg c                                        31

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (13)..(14)
<223> OTHER INFORMATION: a, c, g, t, unknown, or other

<400> SEQUENCE: 22
```
ggcatccgct tcnnscagcc caccaac                                27

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (13)..(14)
<223> OTHER INFORMATION: a, c, g, t, unknown, or other

<400> SEQUENCE: 23
gtctccaagc tcnnsaacac cttccac                                27

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (15)..(16)
<223> OTHER INFORMATION: a, c, g, t, unknown, or other

<400> SEQUENCE: 24
gttaccctcc cggcnnscac tttgacggc                              29

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (13)..(14)
<223> OTHER INFORMATION: a, c, g, t, unknown, or other

<400> SEQUENCE: 25
cgcttcaacc agnnsaccaa ctacttc                                27

<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(15)
<223> OTHER INFORMATION: a, c, g, t, unknown, or other

<400> SEQUENCE: 26
gccgtcgacc ttsnngaggc cgaagcc                                27

<210> SEQ ID NO 27
<211> LENGTH: 28
<212> TYPE: DNA
<213> ORGANISM: Artificial Sequence
<220> FEATURE:
<223> OTHER INFORMATION: Description of Artificial Sequence: Synthetic
      primer <220> FEATURE:
<221> NAME/KEY: modified_base
<222> LOCATION: (14)..(15)
<223> OTHER INFORMATION: a, c, g, t, unknown, or other

<400> SEQUENCE: 27
gtcgcaggca ccsnngaaga ggcggtag                                           28

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(15)
<223> OTHER INFORMATION: a, c, g, t, unknown, or other

<400> SEQUENCE: 28
ctcgttgccg tasnngcagg caccatc                                            27

<210> SEQ ID NO 29
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(15)
<223> OTHER INFORMATION: a, c, g, t, unknown, or other

<400> SEQUENCE: 29
gagggcgacg ggsnngtgga tcaggtag                                           28

<210> SEQ ID NO 30
<211> LENGTH: 31
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (16)..(17)
<223> OTHER INFORMATION: a, c, g, t, unknown, or other

<400> SEQUENCE: 30
gcgtgctcca tgttsnnctc gcggaaagaa g                                       31

<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(15)
<223> OTHER INFORMATION: a, c, g, t, unknown, or other

<400> SEQUENCE: 31
gttggtgggc tgsnngaagc ggatgcc                                            27

<210> SEQ ID NO 32

-continued

```
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(15)
<223> OTHER INFORMATION: a, c, g, t, unknown, or other

<400> SEQUENCE: 32
gtggaaggtg ttsnngagct tggagac                                              27

<210> SEQ ID NO 33
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(15)
<223> OTHER INFORMATION: a, c, g, t, unknown, or other

<400> SEQUENCE: 33
gccgtcaaag tgsnngccgg gagggtaac                                            29

<210> SEQ ID NO 34
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(15)
<223> OTHER INFORMATION: a, c, g, t, unknown, or other

<400> SEQUENCE: 34
gaagtagttg gtsnnctggt tgaagcg                                              27

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (11)..(12)
<223> OTHER INFORMATION: a, c, g, t, unknown, or other

<400> SEQUENCE: 35
cgatctctac nnsatccact cgcc                                                 24

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (13)..(14)
<223> OTHER INFORMATION: a, c, g, t, unknown, or other
```

<400> SEQUENCE: 36
ggcgagtgga tsnngtagag atcg                                          24

<210> SEQ ID NO 37
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (13)..(14)
<223> OTHER INFORMATION: a, c, g, t, unknown, or other

<400> SEQUENCE: 37
gatctctacc agnnscactt ccccgtc                                       27

<210> SEQ ID NO 38
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(15)
<223> OTHER INFORMATION: a, c, g, t, unknown, or other

<400> SEQUENCE: 38
gacggggaag tgsnnctggt agagatc                                       27

<210> SEQ ID NO 39
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (13)..(14)
<223> OTHER INFORMATION: a, c, g, t, unknown, or other

<400> SEQUENCE: 39
ctctaccaga tcnnsttccc cgtcgcc                                       27

<210> SEQ ID NO 40
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(15)
<223> OTHER INFORMATION: a, c, g, t, unknown, or other

<400> SEQUENCE: 40
ggcgacgggg aasnngatct ggtagag                                       27

<210> SEQ ID NO 41
<211> LENGTH: 27
<212> TYPE: DNA
<213> ORGANISM: Artificial Sequence
<220> FEATURE:
<223> OTHER INFORMATION: Description of Artificial Sequence: Synthetic

```
      primer
<220> FEATURE:
<221> NAME/KEY: modified_base
<222> LOCATION: (13)..(14)
<223> OTHER INFORMATION: a, c, g, t, unknown, or other

<400> SEQUENCE: 41
ctcgagtact tcnnsctcta ccagtgc                                              27

<210> SEQ ID NO 42
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (13)..(14)
<223> OTHER INFORMATION: a, c, g, t, unknown, or other

<400> SEQUENCE: 42
gagtacttcg atnnstacca gtgccac                                              27

<210> SEQ ID NO 43
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(15)
<223> OTHER INFORMATION: a, c, g, t, unknown, or other

<400> SEQUENCE: 43
gtacttcgat ctcnnscagt gccacttcc                                            29

<210> SEQ ID NO 44
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (13)..(14)
<223> OTHER INFORMATION: a, c, g, t, unknown, or other

<400> SEQUENCE: 44
ctctaccagt gcnnsttccc cgtcgcc                                              27

<210> SEQ ID NO 45
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(15)
<223> OTHER INFORMATION: a, c, g, t, unknown, or other

<400> SEQUENCE: 45
ctaccagtgc cacnnscccg tcgccctcg                                            29
```

```
<210> SEQ ID NO 46
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (13)..(14)
<223> OTHER INFORMATION: a, c, g, t, unknown, or other

<400> SEQUENCE: 46
cagtgccact tcnnsgtcgc cctcgag                                         27

<210> SEQ ID NO 47
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(15)
<223> OTHER INFORMATION: a, c, g, t, unknown, or other

<400> SEQUENCE: 47
gcactggtag agsnngaagt actcgag                                         27

<210> SEQ ID NO 48
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(15)
<223> OTHER INFORMATION: a, c, g, t, unknown, or other

<400> SEQUENCE: 48
gtggcactgg tasnnatcga agtactc                                         27

<210> SEQ ID NO 49
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (15)..(16)
<223> OTHER INFORMATION: a, c, g, t, unknown, or other

<400> SEQUENCE: 49
ggaagtggca ctgsnngaga tcgaagtac                                       29

<210> SEQ ID NO 50
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(15)
<223> OTHER INFORMATION: a, c, g, t, unknown, or other
```

-continued

<400> SEQUENCE: 50
ggcgacgggg aasnngcact ggtagag                                   27

<210> SEQ ID NO 51
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (15)..(16)
<223> OTHER INFORMATION: a, c, g, t, unknown, or other

<400> SEQUENCE: 51
cgagggcgac gggsnngtgg cactggtag                                 29

<210> SEQ ID NO 52
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(15)
<223> OTHER INFORMATION: a, c, g, t, unknown, or other

<400> SEQUENCE: 52
ctcgagggcg acsnngaagt ggcactg                                   27

<210> SEQ ID NO 53
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (13)..(14)
<223> OTHER INFORMATION: a, c, g, t, unknown, or other

<400> SEQUENCE: 53
gccgactggg gtnnsgagta cttcgatatg                                30

<210> SEQ ID NO 54
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (13)..(14)
<223> OTHER INFORMATION: a, c, g, t, unknown, or other

<400> SEQUENCE: 54
gactggggtc tcnnstactt cgatatg                                   27

<210> SEQ ID NO 55
<211> LENGTH: 30
<212> TYPE: DNA
<213> ORGANISM: Artificial Sequence
<220> FEATURE:

```
<223> OTHER INFORMATION: Description of Artificial Sequence: Synthetic
      primer
<220> FEATURE:
<221> NAME/KEY: modified_base
<222> LOCATION: (14)..(15)
<223> OTHER INFORMATION: a, c, g, t, unknown, or other

<400> SEQUENCE: 55
ctggggtctc gagnnsactt cgatatgtac                                         30

<210> SEQ ID NO 56
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (13)..(14)
<223> OTHER INFORMATION: a, c, g, t, unknown, or other

<400> SEQUENCE: 56
ggtctcgagt acnnsgatat gtaccag                                            27

<210> SEQ ID NO 57
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (13)..(14)
<223> OTHER INFORMATION: a, c, g, t, unknown, or other

<400> SEQUENCE: 57
ctcgagtact tcnnsatgta ccagtgc                                            27

<210> SEQ ID NO 58
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(15)
<223> OTHER INFORMATION: a, c, g, t, unknown, or other

<400> SEQUENCE: 58
gtacttcgat atgnnscagt gccacttcc                                          29

<210> SEQ ID NO 59
<211> LENGTH: 33
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (16)..(17)
<223> OTHER INFORMATION: a, c, g, t, unknown, or other

<400> SEQUENCE: 59
gatatgtacc agtgcnnstt ccccgtcgcc ctc                                     33
```

```
<210> SEQ ID NO 60
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(15)
<223> OTHER INFORMATION: a, c, g, t, unknown, or other

<400> SEQUENCE: 60
gtaccagtgc cacnnscccg tcgccctc                                            28

<210> SEQ ID NO 61
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (13)..(14)
<223> OTHER INFORMATION: a, c, g, t, unknown, or other

<400> SEQUENCE: 61
cacttccccg tcnnsctcga gtacgtc                                             27

<210> SEQ ID NO 62
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(15)
<223> OTHER INFORMATION: a, c, g, t, unknown, or other

<400> SEQUENCE: 62
cttccccgtc gccnnsgagt acgtcgacc                                           29

<210> SEQ ID NO 63
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (13)..(14)
<223> OTHER INFORMATION: a, c, g, t, unknown, or other

<400> SEQUENCE: 63
cccgtcgccc tcnnstacgt cgacccc                                             27

<210> SEQ ID NO 64
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (13)..(14)
```

<223> OTHER INFORMATION: a, c, g, t, unknown, or other

<400> SEQUENCE: 64
gtcgccctcg agnnsgtcga cccctcg          27

<210> SEQ ID NO 65
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (17)..(18)
<223> OTHER INFORMATION: a, c, g, t, unknown, or other

<400> SEQUENCE: 65
catatcgaag tactcsnnac cccagtcggc          30

<210> SEQ ID NO 66
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(15)
<223> OTHER INFORMATION: a, c, g, t, unknown, or other

<400> SEQUENCE: 66
catatcgaag tasnngagac cccagtc          27

<210> SEQ ID NO 67
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (16)..(17)
<223> OTHER INFORMATION: a, c, g, t, unknown, or other

<400> SEQUENCE: 67
gtacatatcg aagtsnnctc gagaccccag          30

<210> SEQ ID NO 68
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(15)
<223> OTHER INFORMATION: a, c, g, t, unknown, or other

<400> SEQUENCE: 68
ctggtacata tcsnngtact cgagacc          27

<210> SEQ ID NO 69
<211> LENGTH: 27
<212> TYPE: DNA
<213> ORGANISM: Artificial Sequence

```
<220> FEATURE:
<223> OTHER INFORMATION: Description of Artificial Sequence: Synthetic
      primer
<220> FEATURE:
<221> NAME/KEY: modified_base
<222> LOCATION: (14)..(15)
<223> OTHER INFORMATION: a, c, g, t, unknown, or other

<400> SEQUENCE: 69
gcactggtac atsnngaagt actcgag                                            27

<210> SEQ ID NO 70
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (15)..(16)
<223> OTHER INFORMATION: a, c, g, t, unknown, or other

<400> SEQUENCE: 70
ggaagtggca ctgsnncata tcgaagtac                                          29

<210> SEQ ID NO 71
<211> LENGTH: 33
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (17)..(18)
<223> OTHER INFORMATION: a, c, g, t, unknown, or other

<400> SEQUENCE: 71
gagggcgacg gggaasnngc actggtacat atc                                     33

<210> SEQ ID NO 72
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(15)
<223> OTHER INFORMATION: a, c, g, t, unknown, or other

<400> SEQUENCE: 72
gagggcgacg ggsnngtggc actggtac                                           28

<210> SEQ ID NO 73
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(15)
<223> OTHER INFORMATION: a, c, g, t, unknown, or other

<400> SEQUENCE: 73
gacgtactcg agsnngacgg ggaagtg                                            27
```

```
<210> SEQ ID NO 74
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE
<221> NAME/KEY: modified_base
<222> LOCATION: (15)..(16)
<223> OTHER INFORMATION: a, c, g, t, unknown, or other

<400> SEQUENCE: 74
ggtcgacgta ctcsnnggcg acggggaag                                29

<210> SEQ ID NO 75
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(15)
<223> OTHER INFORMATION: a, c, g, t, unknown, or other

<400> SEQUENCE: 75
ggggtcgacg tasnngaggg cgacggg                                  27

<210> SEQ ID NO 76
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(15)
<223> OTHER INFORMATION: a, c, g, t, unknown, or other

<400> SEQUENCE: 76 cgagggtcg acsnnctcga gggcgac                                   27

<210> SEQ ID NO 77
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(15)
<223> OTHER INFORMATION: a, c, g, t, unknown, or other

<400> SEQUENCE: 77
gtgccacttc cccnnsgccc tcgagtacg                                29

<210> SEQ ID NO 78
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
```

<222> LOCATION: (15)..(16)
<223> OTHER INFORMATION: a, c, g, t, unknown, or other

<400> SEQUENCE: 78
cgtactcgag ggcsnngggg aagtggcac                           29

<210> SEQ ID NO 79
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (13)..(14)
<223> OTHER INFORMATION: a, c, g, t, unknown, or other

<400> SEQUENCE: 79
gccgactggg gtnnsgagta cttcgatatg                          30

<210> SEQ ID NO 80
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (13)..(14)
<223> OTHER INFORMATION: a, c, g, t, unknown, or other

<400> SEQUENCE: 80
gactggggtc tcnnstactt cgatatg                             27

<210> SEQ ID NO 81
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(15)
<223> OTHER INFORMATION: a, c, g, t, unknown, or other

<400> SEQUENCE: 81
ctggggtctc gagnnsactt cgatatgtac                          30

<210> SEQ ID NO 82
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (13)..(14)
<223> OTHER INFORMATION: a, c, g, t, unknown, or other

<400> SEQUENCE: 82
ggtctcgagt acnnsgatat gtaccag                             27

<210> SEQ ID NO 83
<211> LENGTH: 27
<212> TYPE: DNA

```
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (13)..(14)
<223> OTHER INFORMATION: a, c, g, t, unknown, or other

<400> SEQUENCE: 83
ctcgagtact tcnnsatgta ccagtgc                                           27

<210> SEQ ID NO 84
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(15)
<223> OTHER INFORMATION: a, c, g, t, unknown, or other

<400> SEQUENCE: 84
gtacttcgat atgnnscagt gccacttcc                                         29

<210> SEQ ID NO 85
<211> LENGTH: 33
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (16)..(17)
<223> OTHER INFORMATION: a, c, g, t, unknown, or other

<400> SEQUENCE: 85
gatatgtacc agtgcnnstt ccccgtcgcc ctc                                    33

<210> SEQ ID NO 86
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(15)
<223> OTHER INFORMATION: a, c, g, t, unknown, or other

<400> SEQUENCE: 86
gtaccagtgc cacnnscccg tcgccctc                                          28

<210> SEQ ID NO 87
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (13)..(14)
<223> OTHER INFORMATION: a, c, g, t, unknown, or other

<400> SEQUENCE: 87
```
cacttccccg tcnnsctcga gtacgtc          27

<210> SEQ ID NO 88
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(15)
<223> OTHER INFORMATION: a, c, g, t, unknown, or other

<400> SEQUENCE: 88
cttccccgtc gccnnsgagt acgtcgacc          29

<210> SEQ ID NO 89
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (13)..(14)
<223> OTHER INFORMATION: a, c, g, t, unknown, or other

<400> SEQUENCE: 89
cccgtcgccc tcnnstacgt cgacccc          27

<210> SEQ ID NO 90
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (13)..(14)
<223> OTHER INFORMATION: a, c, g, t, unknown, or other

<400> SEQUENCE: 90
gtcgccctcg agnnsgtcga cccctcg          27

<210> SEQ ID NO 91
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (17)..(18)
<223> OTHER INFORMATION: a, c, g, t, unknown, or other

<400> SEQUENCE: 91
catatcgaag tactcsnnac cccagtcggc          30

<210> SEQ ID NO 92
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:

-continued

```
<221> NAME/KEY: modified_base
<222> LOCATION: (14)..(15)
<223> OTHER INFORMATION: a, c, g, t, unknown, or other

<400> SEQUENCE: 92
catatcgaag tasnngagac cccagtc                                        27

<210> SEQ ID NO 93
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (16)..(17)
<223> OTHER INFORMATION: a, c, g, t, unknown, or other

<400> SEQUENCE: 93
gtacatatcg aagtsnnctc gagacctcag                                     30

<210> SEQ ID NO 94
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(15)
<223> OTHER INFORMATION: a, c, g, t, unknown, or other

<400> SEQUENCE: 94
ctggtacata tcsnngtact cgagacc                                        27

<210> SEQ ID NO 95
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(15)
<223> OTHER INFORMATION: a, c, g, t, unknown, or other

<400> SEQUENCE: 95
gcactggtac atsnngaagt actcgag                                        27

<210> SEQ ID NO 96
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (15)..(16)
<223> OTHER INFORMATION: a, c, g, t, unknown, or other

<400> SEQUENCE: 96
ggaagtggca ctgsnncata tcgaagtac                                      29

<210> SEQ ID NO 97
<211> LENGTH: 33
```

-continued

```
<212> TYPE: DNA
<213> ORGANISM: Artificial Sequence
<220> FEATURE:
<223> OTHER INFORMATION: Description of Artificial Sequence: Synthetic
      primer
<220> FEATURE
<221> NAME/KEY: modified_base
<222> LOCATION: (17)..(18)
<223> OTHER INFORMATION: a, c, g, t, unknown, or other

<400> SEQUENCE: 97
gagggcgacg gggaasnngc actggtacat atc                                    33

<210> SEQ ID NO 98
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(15)
<223> OTHER INFORMATION: a, c, g, t, unknown, or other

<400> SEQUENCE: 98
gagggcgacg ggsnngtggc actggtac                                          28

<210> SEQ ID NO 99
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(15)
<223> OTHER INFORMATION: a, c, g, t, unknown, or other

<400> SEQUENCE: 99
gacgtactcg agsnngacgg ggaagtg                                           27

<210> SEQ ID NO 100
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (15)..(16)
<223> OTHER INFORMATION: a, c, g, t, unknown, or other

<400> SEQUENCE: 100
ggtcgacgta ctcsnnggcg acggggaag                                         29

<210> SEQ ID NO 101
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(15)
<223> OTHER INFORMATION: a, c, g, t, unknown, or other

<400> SEQUENCE: 101
```

```
ggggtcgacg tasnngaggg cgacggg                                      27
```

<210> SEQ ID NO 102
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(15)
<223> OTHER INFORMATION: a, c, g, t, unknown, or other

<400> SEQUENCE: 102

```
cgaggggtcg acsnnctcga gggcgac                                      27
```

<210> SEQ ID NO 103
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103

```
ggatctcgac gctctccct                                               19
```

<210> SEQ ID NO 104
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104

```
gctagttatt gctcagcgg                                               19
```

<210> SEQ ID NO 105
<211> LENGTH: 49
<212> TYPE: PRT
<213> ORGANISM: Candida tenuis

<400> SEQUENCE: 105

Asp Leu Lys Val Asp Tyr Val Asp Leu Phe Leu Ile His Phe Pro Ile
 1               5                  10                  15

Ala Phe Lys Phe Val Pro Ile Glu Glu Lys Tyr Pro Pro Gly Phe Tyr
             20                  25                  30

Cys Gly Asp Gly Asn Asn Phe Val Tyr Glu Asp Val Pro Ile Leu Glu
         35                  40                  45

Thr

<210> SEQ ID NO 106
<211> LENGTH: 49
<212> TYPE: PRT
<213> ORGANISM: Pichia stipitis

<400> SEQUENCE: 106

Asp Leu Gln Val Asp Tyr Val Asp Leu Phe Leu Ile His Phe Pro Val
 1               5                  10                  15

Thr Phe Lys Phe Val Pro Leu Glu Glu Lys Tyr Pro Pro Gly Phe Tyr
             20                  25                  30

```
Cys Gly Lys Gly Asp Asn Phe Asp Tyr Glu Asp Val Pro Ile Leu Glu
        35                  40                  45

Thr
```

<210> SEQ ID NO 107
<211> LENGTH: 49
<212> TYPE: PRT
<213> ORGANISM: Candida tropicalis

<400> SEQUENCE: 107

```
Asp Leu Asn Leu Asp Tyr Val Asp Leu Phe Leu Ile His Phe Pro Ile
 1               5                  10                  15

Ala Phe Lys Phe Val Pro Ile Glu Glu Lys Tyr Pro Pro Gly Phe Tyr
            20                  25                  30

Cys Gly Asp Gly Asp Asn Phe His Tyr Glu Asp Val Pro Leu Leu Asp
        35                  40                  45

Thr
```

<210> SEQ ID NO 108
<211> LENGTH: 49
<212> TYPE: PRT
<213> ORGANISM: Candida albicans

<400> SEQUENCE: 108

```
Asp Leu Asn Leu Glu Tyr Leu Asp Leu Phe Leu Ile His Phe Pro Ile
 1               5                  10                  15

Ala Phe Lys Phe Val Pro Leu Glu Glu Lys Tyr Pro Pro Gly Phe Tyr
            20                  25                  30

Cys Gly Asp Gly Asp Lys Phe His Tyr Glu Asn Val Pro Leu Leu Asp
        35                  40                  45

Thr
```

<210> SEQ ID NO 109
<211> LENGTH: 49
<212> TYPE: PRT
<213> ORGANISM: Pichia guilliermondii

<400> SEQUENCE: 109

```
Asp Leu Lys Val Asp Tyr Leu Asp Leu Phe Leu Ile His Phe Pro Ile
 1               5                  10                  15

Ala Phe Lys Phe Val Pro Phe Glu Glu Lys Tyr Pro Pro Gly Phe Tyr
            20                  25                  30

Cys Gly Asp Gly Asp Lys Phe Thr Tyr Glu Asp Val Pro Ile Ile Asp
        35                  40                  45

Thr
```

<210> SEQ ID NO 110
<211> LENGTH: 48
<212> TYPE: PRT
<213> ORGANISM: Aspergillus niger

<400> SEQUENCE: 110

```
Asp Trp Gly Ile Asp Tyr Phe Asp Leu Tyr Ile Val His Phe Pro Ile
 1               5                  10                  15

Ser Leu Lys Tyr Val Asp Pro Ala Val Arg Tyr Pro Pro Gly Trp Lys
            20                  25                  30

Ser Glu Lys Asp Glu Leu Glu Phe Gly Asn Ala Thr Ile Gln Glu Thr
        35                  40                  45
```

<210> SEQ ID NO 111
<211> LENGTH: 49
<212> TYPE: PRT
<213> ORGANISM: Aspergillus terreus

<400> SEQUENCE: 111

Asp Trp Gly Val Asp Tyr Phe Asp Leu Tyr Ile Val His Phe Pro Val
1               5                   10                  15

Ala Leu Lys Tyr Val Asp Pro Ala Val Arg Tyr Pro Pro Gly Trp Ser
            20                  25                  30

Ala Lys Gly Asp Gly Ser Ile Glu Phe Ser Asn Ala Ser Ile Gln Glu
        35                  40                  45

Thr

<210> SEQ ID NO 112
<211> LENGTH: 50
<212> TYPE: PRT
<213> ORGANISM: Hypocrea jecorina

<400> SEQUENCE: 112

Asp Trp Gln Ile Asp Tyr Phe Asp Leu Phe Leu Val His Phe Pro Ala
1               5                   10                  15

Ala Leu Glu Tyr Val Asp Pro Ser Val Arg Tyr Pro Pro Gly Trp Phe
            20                  25                  30

Tyr Asp Gly Lys Ser Glu Val Arg Trp Ser Lys Thr Thr Thr Leu Gln
        35                  40                  45

Gln Thr
    50

<210> SEQ ID NO 113
<211> LENGTH: 49
<212> TYPE: PRT
<213> ORGANISM: Neurospora crassa

<400> SEQUENCE: 113

Asp Trp Gly Val Glu Tyr Phe Asp Met Tyr Gln Cys His Phe Pro Ile
1               5                   10                  15

Ala Leu Glu Tyr Val Asp Pro Ser Val Arg Tyr Pro Pro Gly Trp His
            20                  25                  30

Phe Asp Gly Lys Ser Glu Ile Arg Pro Ser Lys Ala Thr Ile Gln Glu
        35                  40                  45

Thr

<210> SEQ ID NO 114
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 114

His His His His His His
1               5

<210> SEQ ID NO 115
<211> LENGTH: 969
<212> TYPE: DNA
<213> ORGANISM: Neurospora crassa

<400> SEQUENCE: 115

```
atggttcctg ctatcaagct caactccggc ttcgacatgc cccaggtcgg cttcggcctc      60
tggaaggtcg acggctccat cgcttccgat gtcgtctaca acgctatcaa ggcaggctac     120
cgcctcttcg atggtgcctg cgactacggc aacgaggttg agtgcggcca gggtgtagcc     180
cgcgccatca aggagggcat cgtcaagcgc gaggagctct ttatcgtctc caagctctgg     240
aacaccttcc acgacggcga ccgcgtcgag cccatcgtcc gcaagcagct tgccgactgg     300
ggtgtggagt acttcgatat gtaccagtgc cacttcccca tcgccctcga gtacgtcgac     360
ccctcggtcc gttaccctcc cggctggcac tttgacggca agagcgagat ccgcccctcc     420
aaggccacca tccaagagac ctggacggcc atggagtcgc tcgtcgagaa gggtctctcc     480
aagagcattg gcgtctccaa cttccaggcc cagctcctgt acgacctcct ccgctacgcc     540
aaggtccgcc ccgccactct ccagatcgag caccacccct acctcgtcca gcagaacctc     600
ctcaaccttg ccaaggctga gggcatcgcc gtgaccgcct actcctcctt cggccctgct     660
tctttccgcg agttcaacat ggagcacgcc cagaagctcc agcctctcct cgaggacccc     720
accatcaagg ctattggtga caagtacaac aaggatcctg cccaggtcct cctccgttgg     780
gccacccagc gcggcctggc catcatcccc aagtctagcc gcgaggccac catgaagtcc     840
aacctcaact ctcttgattt cgatctctcc gaggaggaca tcaagaccat ctctggtttc     900
gaccgcggca tccgcttcaa ccagcccacc aactacttct ccgccgagaa cctctggatt     960
ttcggttag                                                             969

<210> SEQ ID NO 116
<211> LENGTH: 969
<212> TYPE: DNA
<213> ORGANISM: Neurospora crassa

<400> SEQUENCE: 116
atggttcctg ctatcaagct caactccggc ttcgacatgc cccaggtcgg cttcggcctc      60
tggaaggtcg acggctccat cgcttccgat gtcgtctaca acgctatcaa ggcaggctac     120
cgcctcttcg atggtgcctg cgactacggc aacgaggttg agtgcggcca gggtgtagcc     180
cgcgccatca aggagggcat cgtcaagcgc gaggagctct ttatcgtctc caagctctgg     240
aacaccttcc acgacggcga ccgcgtcgag cccatcgtcc gcaagcagct tgccgactgg     300
ggtctcgagt acttcgatct ctacctgatc cactcgcccg tcgccctcga gtacgtcgac     360
ccctcggtcc gttaccctcc cggctggcac tttgacggca agagcgagat ccgcccctcc     420
aaggccacca tccaagagac ctggacggcc atggagtcgc tcgtcgagaa gggtctctcc     480
aagagcattg gcgtctccaa cttccaggcc cagctcctgt acgacctcct ccgctacgcc     540
aaggtccgcc ccgccactct ccagatcgag caccacccct acctcgtcca gcagaacctc     600
ctcaaccttg ccaaggctga gggcatcgcc gtgaccgcct actcctcctt cggccctgct     660
tctttccgcg agttcaacat ggagcacgcc cagaagctcc agcctctcct cgaggacccc     720
accatcaagg ctattggtga caagtacaac aaggatcctg cccaggtcct cctccgttgg     780
gccacccagc gcggcctggc catcatcccc aagtctagcc gcgaggccac catgaagtcc     840
aacctcaact ctcttgattt cgatctctcc gaggaggaca tcaagaccat ctctggtttc     900
gaccgcggca tccgcttcaa ccagcccacc aactacttct ccgctgagaa cctctggatt     960
ttcggttag                                                             969
```